(12) United States Patent
Kaplan et al.

(10) Patent No.: US 11,891,350 B2
(45) Date of Patent: Feb. 6, 2024

(54) COMPOUNDS FOR USE IN THE TREATMENT OR PROPHYLAXIS OF PAIN, INFLAMMATION AND/OR AUTOIMMUNITY

(71) Applicant: NOVAREMED LTD., Petah Tikva (IL)

(72) Inventors: Eli Kaplan, Basel (CH); Robert Hett, Basel (CH)

(73) Assignee: Novaremed Ltd., Petah Tikva (IL)

( * ) Notice: Subject to any disclaimer, the term of this patent is extended or adjusted under 35 U.S.C. 154(b) by 490 days.

(21) Appl. No.: 17/295,788

(22) PCT Filed: Jan. 22, 2020

(86) PCT No.: PCT/EP2020/051528
§ 371 (c)(1),
(2) Date: May 20, 2021

(87) PCT Pub. No.: WO2020/152226
PCT Pub. Date: Jul. 30, 2020

(65) Prior Publication Data
US 2022/0002228 A1   Jan. 6, 2022

(30) Foreign Application Priority Data

Jan. 23, 2019 (EP) .................... 19153315

(51) Int. Cl.
*C07C 233/22* (2006.01)

(52) U.S. Cl.
CPC ........ *C07C 233/22* (2013.01); *C07B 2200/13* (2013.01); *C07C 2601/16* (2017.05)

(58) Field of Classification Search
CPC ................ C07C 233/22; C07B 2200/13
See application file for complete search history.

(56) References Cited

U.S. PATENT DOCUMENTS

| | | |
|---|---|---|
| 7,642,290 B2 | 1/2010 | Kaplan |
| 7,674,829 B2 | 3/2010 | Kaplan |
| 7,754,771 B2 | 7/2010 | Kaplan |
| 8,252,843 B2 | 8/2012 | Kaplan |
| 8,802,734 B2 | 8/2014 | Kaplan |
| 8,883,853 B2 | 11/2014 | Kaplan |
| 9,199,917 B2 | 12/2015 | Kaplan |
| 9,381,173 B2 | 7/2016 | Kaplan |
| 2011/0086910 A1 | 4/2011 | Kaplan |

FOREIGN PATENT DOCUMENTS

| | | |
|---|---|---|
| WO | 2011/030205 A1 | 3/2011 |
| WO | 2013/084238 A1 | 6/2013 |

OTHER PUBLICATIONS

PCT/EP2020/051528, International Search Report, dated Jul. 4, 2020.
PCT/EP2020/051528, Written Opinion of the International Searching Authority, dated Jul. 4, 2020.
PCT/EP2020/051528, International Preliminary Report on Patentability (Chapter II), dated Apr. 26, 2021.
Indian Application No. 202117022440, Examination Report, dated Feb. 24, 2022.
European Application No. 20703152.7, Decision to grant a European patent pursuant to Article 97(1) EPC, dated Apr. 7, 2022.

*Primary Examiner* — Sikarl A Witherspoon
(74) *Attorney, Agent, or Firm* — Allan A. Fanucci

(57) ABSTRACT

The present invention relates to a polymorphic form of (S,S)-2-N(3-O-(propan-2-ol)-1-propyl-4-hydroxybenzene)-3-phenylpropylamide or synonymously named N-[2-(4-Hydroxy-phenyl)-(2-hydroxy-propoxymethyl)-ethyl]-3-phenyl-propionamide and to the treatment or prophylaxis of pain, inflammation and/or autoimmunity and provides a method of treating or preventing pain, inflammation and/or autoimmunity as well as the use of this polymorphic form in the manufacture of medicaments for the treatment or prophylaxis of pain (preferably nociceptive or neuropathic), inflammation and/or autoimmunity in humans and/or non-human animals.

22 Claims, 17 Drawing Sheets

Analytical Data Sheet

| Product Code | NRD135 S E1 Form 1 |
|---|---|
| Batch No. | RM1407-269 (141232)-M |
| Batch Quantity | 1.7 kg (2014 Regis, Micron) |
| Storage Conditions | Store below 25°C |
| Shipping Conditions | Ship below 30°C |
| Retest Date | August 2019 |
| Restriction | not for human use |
| Structure: | 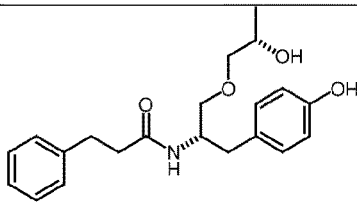 NRD135 S E1 $C_{21}H_{27}NO_4$ Mol. Wt.: 357,44 |

Analytical Data

| Attribute | Method | Result |
|---|---|---|
| Appearance | visual | white powder* |
| Assay | HPLC | 98.1%* |
| Identity | NMR | conforms to structure* |
|  | DSC | conforms to Form 1** |
| PSD | Laser Diffraction | $D_{90}$ 3 µm*** |
|  |  | $D_{100}$ 9 µm*** |

*based on Regis CoA dated 14-Dec-2017based on data obtained by Solid Chem
**based on Pharmaterial/Quotient Results
***based on Micron results (I 5 $2^{nd}$ pass)

Fig. 5

| | Analytical Data Sheet |
|---|---|

| Product Code | NRD135 S E1 Form 2 |
|---|---|
| Batch No. | COEN 4-091-M |
| Batch Quantity | 80 g |
| Storage Conditions | Store below 25°C |
| Shipping Conditions | Ship below 30°C |
| Retest Date | August 2019 |
| Restriction | not for human use |
| Structure: | NRD135 S E1<br>$C_{21}H_{27}NO_4$<br>Mol. Wt.: 357,44 |

Analytical Data

| Attribute | Method | Result |
|---|---|---|
| Appearance | visual | white powder* |
| Assay (Potency) | HPLC | 98.7%** |
| Identity | NMR | conforms to structure** |
| | DSC | conforms to Form 2*** |
| PSD | Laser Diffraction | D90 10 µm* |
| | | D100 19 µm* |

\* based on data obtained from MCKO
\*\* based on tests performed on the unmicronised material AR-115956 DRL
\*\*\*based on data obtained by Solid Chem Basel, Date   30 Jul 2018

Robert Hett QA consultant for Novaremed

Fig. 6

| Week | Sequence – Period Treatment | Material Batch ID | Dose Route | Target Dose Level (mg/kg) | Animal ID | Animal Bodyweight (kg) | Weight of Dose Administered (g) | Calculated Dose Concentration (mg/mL)$^A$ | Calculated 'mg' Received (mg)$^B$ | Calculated Dose Level (mg/kg)$^B$ | % Difference from Target |
|---|---|---|---|---|---|---|---|---|---|---|---|
| 1 | 1-1 Old | 141232 | PO | 60 | 001M | 11.5 | 58.4 | 12.0 | 701 | 61.0 | 1.6 |
| | | | | | 002M | 10.6 | 54.2 | 12.0 | 651 | 61.4 | 2.3 |
| | | | | | 003M | 11.4 | 57.8 | 12.0 | 693 | 60.6 | 1.0 |
| | 2-1 New | COEN4_091-M | PO | 60 | 004M | 11.0 | 54.9 | 12.3 | 675 | 61.6 | 2.7 |
| | | | | | 005M | 10.6 | 53.4 | 12.3 | 657 | 62.0 | 3.3 |
| | | | | | 006M | 9.59 | 48.5 | 12.3 | 596 | 62.2 | 3.6 |
| 2 | 1-2 New | COEN4-091-M | PO | 60 | 001M | 11.5 | 56.9 | 12.8 | 728 | 63.5 | 5.8 |
| | | | | | 002M | 10.9 | 53.9 | 12.8 | 689 | 63.4 | 5.6 |
| | | | | | 003M | 11.4 | 56.6 | 12.8 | 724 | 63.8 | 6.3 |
| | 2-2 Old | 141232 | PO | 60 | 004M | 10.9 | 53.4 | 12.3 | 656 | 60.3 | 0.5 |
| | | | | | 005M | 10.2 | 51.8 | 12.3 | 637 | 62.4 | 4.0 |
| | | | | | 006M | 9.54 | 47.3 | 12.3 | 582 | 61.0 | 1.7 |

Fig. 7

| Week | Sequence – Period Treatment | Material Batch ID | Dose Route | Target Dose Level (mg/kg) | Animal ID | Target Blood Sampling Times (minutes after dosing) | | | | | | | | | |
|------|------|------|------|------|------|------|------|------|------|------|------|------|------|------|------|
| | | | | | | 15 | 30 | 60 | 120 | 180 | 240 | 360 | 480 | 720 | 1500 |
| | | | | | | Actual Blood Sampling Times (minutes after dosing) | | | | | | | | | |
| 1 | 1-1 Old | 141232 | PO | 60 | 001M | 16 | 30 | 60 | 120 | 180 | 240 | 360 | 474 | 720 | 1500 |
| | | | | | 002M | 16 | 30 | 60 | 120 | 180 | 240 | 360 | 474 | 720 | 1500 |
| | | | | | 003M | 16 | 30 | 60 | 120 | 180 | 240 | 360 | 475 | 720 | 1500 |
| | 2-1 New | COEN4_091-M | PO | 60 | 004M | 16 | 30 | 60 | 120 | 180 | 241 | 360 | 475 | 720 | 1500 |
| | | | | | 005M | 16 | 30 | 60 | 120 | 180 | 241 | 360 | 475 | 720 | 1500 |
| | | | | | 006M | 15 | 30 | 60 | 120 | 180 | 241 | 360 | 475 | 720 | 1500 |
| 2 | 1-2 New | COEN4-091-M | PO | 60 | 001M | 15 | 30 | 60 | 120 | 180 | 240 | 360 | 480 | 720 | 1504 |
| | | | | | 002M | 15 | 30 | 60 | 120 | 180 | 240 | 360 | 480 | 720 | 1504 |
| | | | | | 003M | 15 | 30 | 60 | 121 | 180 | 240 | 360 | 480 | 720 | 1504 |
| | 2-2 Old | 141232 | PO | 60 | 004M | 15 | 30 | 60 | 122 | 180 | 240 | 361 | 480 | 720 | 1504 |
| | | | | | 005M | 15 | 30 | 60 | 122 | 180 | 240 | 361 | 480 | 720 | 1504 |
| | | | | | 006M | 15 | 30 | 60 | 122 | 180 | 240 | 361 | 480 | 720 | 1504 |

Fig. 8

| Week | Sequence – Period Treatment | Material Batch ID | Dose Route | Target Dose Level (mg/kg) | Animal ID | Concentration of NRD135S.E1 in dog plasma (ng/mL) | | | | | | | | | | |
|---|---|---|---|---|---|---|---|---|---|---|---|---|---|---|---|---|
| | | | | | | Timepoint (h) | | | | | | | | | | |
| | | | | | | 0 | 0.25 | 0.5 | 1 | 2 | 3 | 4 | 6 | 8 | 12 | 24 |
| 1 | 1-1 Old | 141232 | PO | 60 | 001M | <LLOQ | 4527 | 3857 | 1893 | 557 | 306 | 198 | 276 | 369 | 215 | 54.6 |
| | | | | | 002M | <LLOQ | 8012 | 5944 | 4288 | 1209 | 799 | 663 | 660 | 805 | 831 | 61.3 |
| | | | | | 003M | <LLOQ | 5458 | 4378 | 3753 | 1286 | 806 | 560 | 778 | 550 | 532 | 67.4 |
| | Mean | | | | | <LLOQ | 5999 | 4726 | 3311 | 1017 | 637 | 474 | 572 | 575 | 526 | 61.1 |
| | SD | | | | | NA | 1804 | 1086 | 1257 | 401 | 287 | 244 | 263 | 219 | 308 | 6.43 |
| | 2-1 New | COEN4_091-M | PO | 60 | 004M | <LLOQ | 3250 | 10110 | 5813 | 1065 | 463 | 335 | 647 | 635 | 337 | 56.4 |
| | | | | | 005M | <LLOQ | 9680 | 7690 | 3392 | 1180 | 462 | 436 | 347 | 463 | 748 | 160 |
| | | | | | 006M | <LLOQ | 8938 | 7459 | 4424 | 673 | 239 | 205 | 694 | 567 | 371 | 30.3 |
| | Mean | | | | | <LLOQ | 7289 | 8419 | 4543 | 973 | 388 | 325 | 563 | 555 | 485 | 82.3 |
| | SD | | | | | NA | 3518 | 1469 | 1215 | 266 | 129 | 116 | 188 | 86.6 | 228 | 68.7 |
| 2 | 1-2 New | COEN4-091-M | PO | 60 | 001M | <LLOQ | 13817 | 9588 | 3511 | 618 | 264 | 284 | 448 | 422 | 342 | 24.4 |
| | | | | | 002M | <LLOQ | 15044 | 11333 | 7578 | 1690 | 518 | 416 | 784 | 1028 | 1173 | 94.4 |
| | | | | | 003M | <LLOQ | 12771 | 13336 | 7486 | 1698 | 541 | 329 | 459 | 614 | 635 | 137 |
| | Mean | | | | | <LLOQ | 13877 | 11419 | 6192 | 1335 | 441 | 343 | 564 | 688 | 717 | 85.2 |
| | SD | | | | | NA | 1137 | 1875 | 2322 | 622 | 154 | 67.2 | 191 | 309 | 422 | 56.7 |
| | 2-2 Old | 141232 | PO | 60 | 004M | <LLOQ | 2105 | 4169 | 2431 | 576 | 245 | 162 | 294 | 326 | 286 | 26.8 |
| | | | | | 005M | <LLOQ | 3633 | 5741 | 2958 | 997 | 711 | 377 | 527 | 611 | 575 | 13.3 |
| | | | | | 006M | <LLOQ | 3612 | 3287 | 1956 | 1147 | 543 | 248 | 251 | 392 | 432 | 19.5 |
| | Mean | | | | | <LLOQ | 3116 | 4399 | 2448 | 907 | 499 | 262 | 358 | 443 | 431 | 19.9 |
| | SD | | | | | NA | 876 | 1243 | 501 | 296 | 236 | 108 | 148 | 149 | 145 | 6.74 |

Fig. 9

| Sequence | Polymorph ID | Animal ID | Actual dose (mg/kg) | Animal weight (kg) | Tmax (h) | Cmax (ng/mL) | AUC(0-t) (h*ng/mL) | AUC(0-∞) (h*ng/mL) | AUCext (%) | CL/F (mL/h/kg) | V/F (mL/kg) | T1/2 (h) |
|---|---|---|---|---|---|---|---|---|---|---|---|---|
| 1-1 Old | 141232 | 001M | 60.98 | 11.5 | 0.25 | 4530 | 9000 | 9500 | 5.19 | 6420 | 58000 | 6.26 |
| | | 002M | 61.4 | 10.6 | 0.25 | 8010 | 21600 | 22000 | 1.39 | 2800 | 13900 | 3.46 |
| | | 003M | 60.6 | 11.4 | 0.25 | 5460 | 16900 | 17300 | 2.45 | 3490 | 22000 | 4.36 |
| | | | | n | 3 | 3 | 3 | 3 | 3 | 3 | 3 | 3 |
| | | | | Arithmetic Mean* | 0.25 | 6000 | 15900 | 16300 | 3.01 | 4240 | 31300 | 4.69 |
| | | | | SD | - | 1800 | 6390 | 6300 | 1.96 | 1920 | 23500 | 1.43 |
| | | | | SE | - | 1040 | 3690 | 3640 | 1.13 | 1110 | 13500 | 0.826 |
| | | | | Min | - | 4530 | 9000 | 9500 | 1.39 | 2800 | 13900 | 3.46 |
| | | | | Max | - | 8010 | 21600 | 22000 | 5.19 | 6420 | 58000 | 6.26 |
| | | | | CV% | - | 30.1 | 40.3 | 38.7 | 65.1 | 45.4 | 74.9 | 30.5 |
| | | | | Geometric Mean | - | 5830 | 14900 | 15300 | 2.60 | 3970 | 26100 | 4.55 |
| | | | | CI 95% Lower | - | -1760 | -11600 | -10800 | -5.43 | -4040 | -69600 | -1.46 |
| | | | | CI 95% Upper | - | 13800 | 43300 | 43400 | 11.4 | 12500 | 132000 | 10.8 |
| 2-1 New | COEN4-091-M | 004M | 61.61 | 11.0 | 0.5 | 10100 | 17400 | 17800 | 2.25 | 3460 | 24500 | 4.91 |
| | | 005M | 61.96 | 10.6 | 0.25 | 9680 | 19600 | 21000 | 6.45 | 2950 | 24900 | 5.85 |
| | | 006M | 62.17 | 9.59 | 0.25 | 8940 | 16000 | 16200 | 0.975 | 3850 | 20000 | 3.60 |
| | | | | n | 3 | 3 | 3 | 3 | 3 | 3 | 3 | 3 |
| | | | | Arithmetic Mean* | 0.25 | 9580 | 17700 | 18300 | 3.22 | 3420 | 23100 | 4.79 |
| | | | | SD | - | 593 | 1820 | 2450 | 2.86 | 448 | 2740 | 1.13 |
| | | | | SE | - | 342 | 1050 | 1410 | 1.65 | 259 | 1580 | 0.652 |
| | | | | Min | - | 8940 | 16000 | 16200 | 0.975 | 2950 | 20000 | 3.60 |
| | | | | Max | - | 10100 | 19600 | 21000 | 6.45 | 3850 | 24900 | 5.85 |
| | | | | CV% | - | 6.19 | 10.3 | 13.4 | 88.9 | 13.1 | 11.8 | 23.6 |
| | | | | Geometric Mean | - | 9560 | 17600 | 18200 | 2.42 | 3400 | 23000 | 4.69 |
| | | | | CI 95% Lower | - | 7030 | 9830 | 7790 | -9.10 | 1490 | 11300 | -0.0727 |
| | | | | CI 95% Upper | - | 12100 | 25500 | 28800 | 15.5 | 5350 | 34900 | 9.65 |

Fig. 10

| Sequence | Polymorph ID | Animal ID | Actual dose (mg/kg) | Animal weight (kg) | Tmax (h) | Cmax (ng/mL) | AUC(0-t) (h*ng/mL) | AUC(0-∞) (h*ng/mL) | AUCext (%) | CL/F (mL/h/kg) | V/F (mL/kg) | T1/2 (h) |
|---|---|---|---|---|---|---|---|---|---|---|---|---|
| 1-2 New | COEN4-091-M | 001M | 63.47 | 11.5 | 0.25 | 13800 | 16200 | 16300 | 0.737 | 3880 | 19100 | 3.42 |
| | | 002M | 63.35 | 10.9 | 0.25 | 15000 | 31800 | 32200 | 1.51 | 1960 | 10100 | 3.58 |
| | | 003M | 63.81 | 11.4 | 0.5 | 13300 | 25600 | 26700 | 4.32 | 2390 | 20200 | 5.86 |
| | | n | | | 3 | 3 | 3 | 3 | 3 | 3 | 3 | 3 |
| | | Arithmetic Mean* | | | 0.25 | 14100 | 24500 | 25100 | 2.19 | 2740 | 16500 | 4.29 |
| | | SD | | | - | 881 | 7830 | 8080 | 1.89 | 1010 | 5520 | 1.37 |
| | | SE | | | - | 508 | 4520 | 4670 | 1.09 | 583 | 3190 | 0.790 |
| | | Min | | | - | 13300 | 16200 | 16300 | 0.737 | 1960 | 10100 | 3.42 |
| | | Max | | | - | 15000 | 31800 | 32200 | 4.32 | 3880 | 20200 | 5.86 |
| | | CV% | | | - | 6.26 | 31.9 | 32.2 | 86.1 | 36.8 | 33.5 | 32.0 |
| | | Geometric Mean | | | - | 14000 | 23600 | 24200 | 1.69 | 2630 | 15800 | 4.15 |
| | | CI 95% Lower | | | - | 10300 | -9150 | -9660 | -5.93 | -1600 | -7290 | -1.61 |
| | | CI 95% Upper | | | - | 17900 | 58200 | 59900 | 10.3 | 7090 | 40300 | 10.2 |
| 2-2 Old | 141232 | 004M | 60.33 | 10.9 | 0.5 | 4170 | 9150 | 9300 | 1.58 | 6490 | 35600 | 3.80 |
| | | 005M | 62.37 | 10.2 | 0.5 | 5740 | 15400 | 15500 | 0.298 | 4030 | 13900 | 2.39 |
| | | 006M | 61.03 | 9.50 | 0.25 | 3610 | 11100 | 11200 | 0.728 | 5440 | 22800 | 2.91 |
| | | n | | | 3 | 3 | 3 | 3 | 3 | 3 | 3 | 3 |
| | | Arithmetic Mean* | | | 0.5 | 4510 | 11900 | 12000 | 0.869 | 5320 | 24100 | 3.04 |
| | | SD | | | - | 1100 | 3200 | 3150 | 0.654 | 1230 | 10900 | 0.714 |
| | | SE | | | - | 638 | 1850 | 1820 | 0.377 | 711 | 6300 | 0.412 |
| | | Min | | | - | 3610 | 9150 | 9300 | 0.298 | 4030 | 13900 | 2.39 |
| | | Max | | | - | 5740 | 15400 | 15500 | 1.58 | 6490 | 35600 | 3.8 |
| | | CV% | | | - | 24.5 | 26.9 | 26.3 | 75.2 | 23.2 | 45.2 | 23.5 |
| | | Geometric Mean | | | - | 4420 | 11600 | 11700 | 0.700 | 5220 | 22500 | 2.98 |
| | | CI 95% Lower | | | - | -245 | -1870 | -1580 | -1.94 | 18.4 | -22800 | -0.0379 |
| | | CI 95% Upper | | | - | 9260 | 25700 | 25600 | 3.68 | 10600 | 71000 | 6.11 |

Fig.11

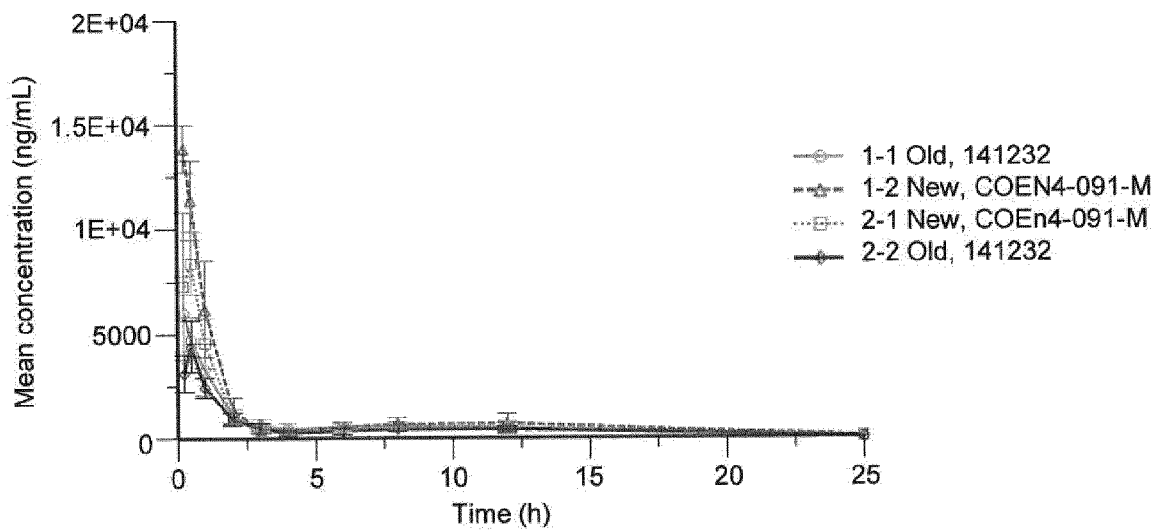
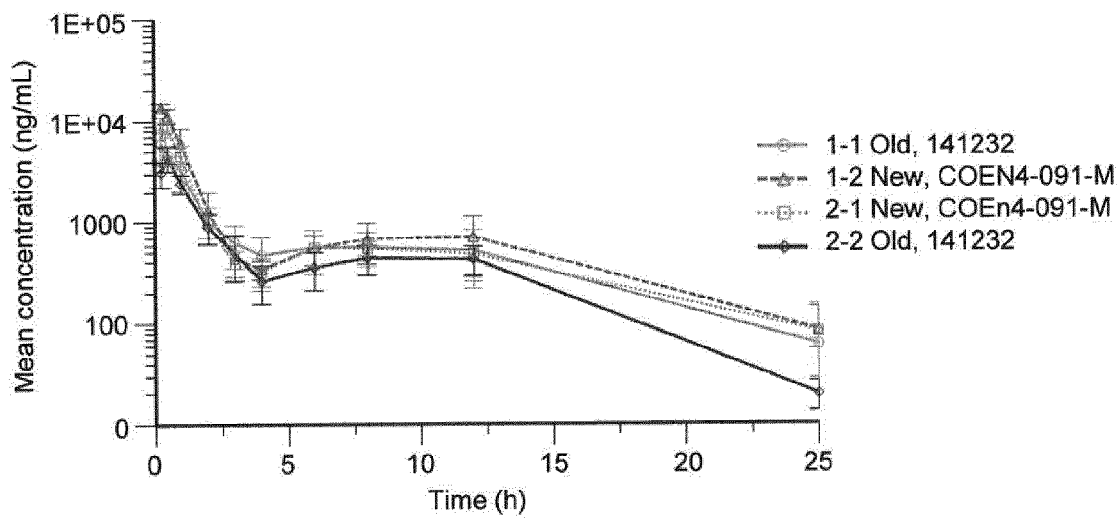
Fig. 12

A
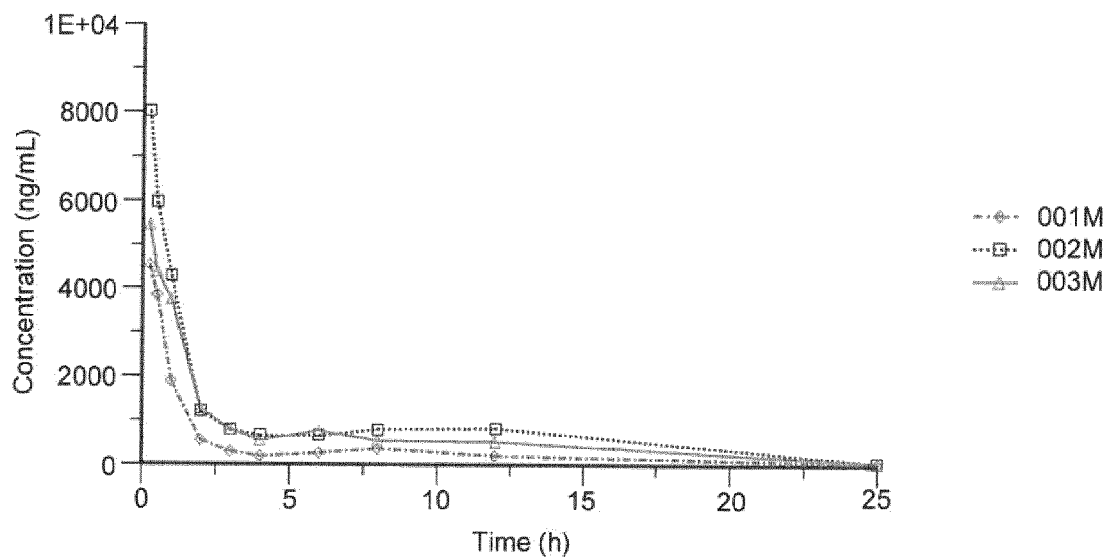
B
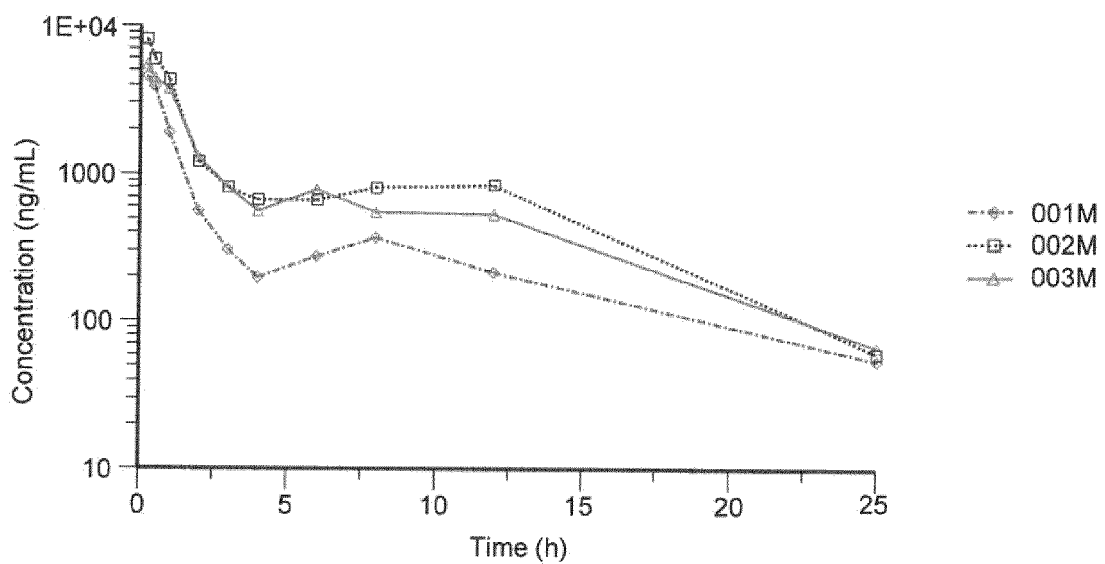
Fig. 13

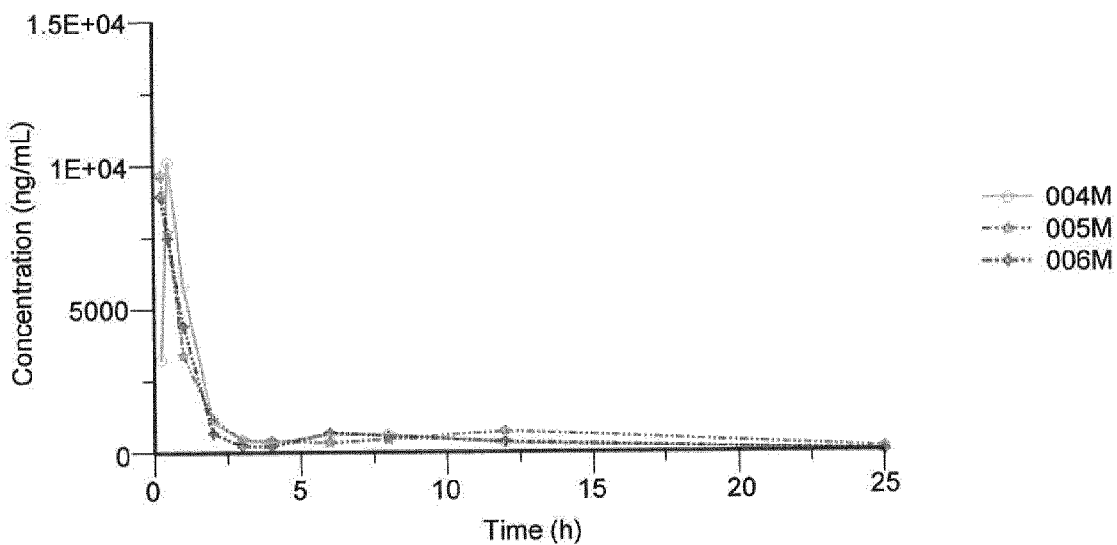
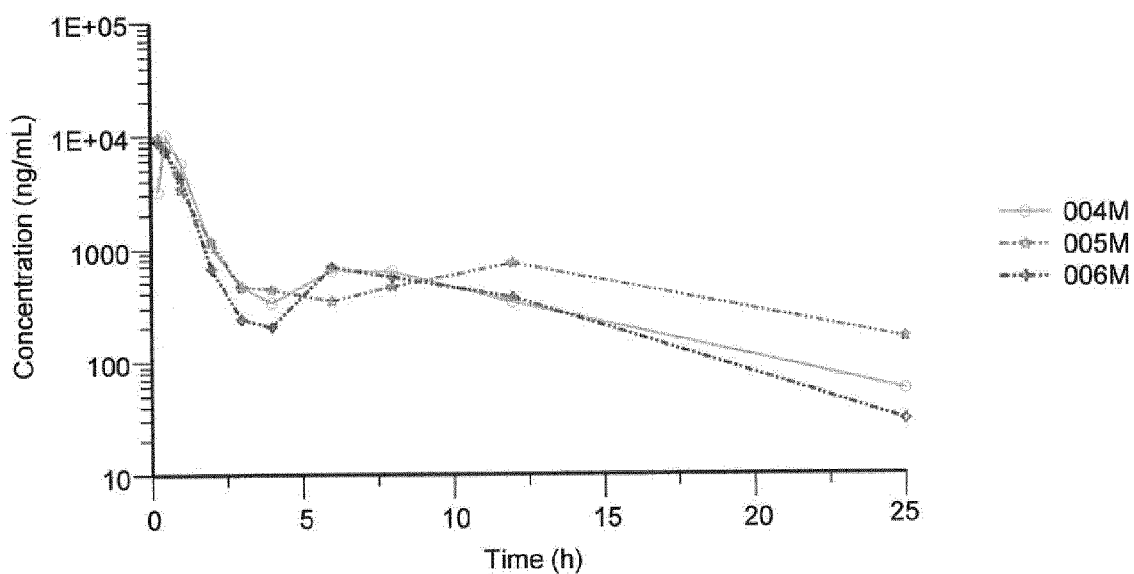
Fig. 14

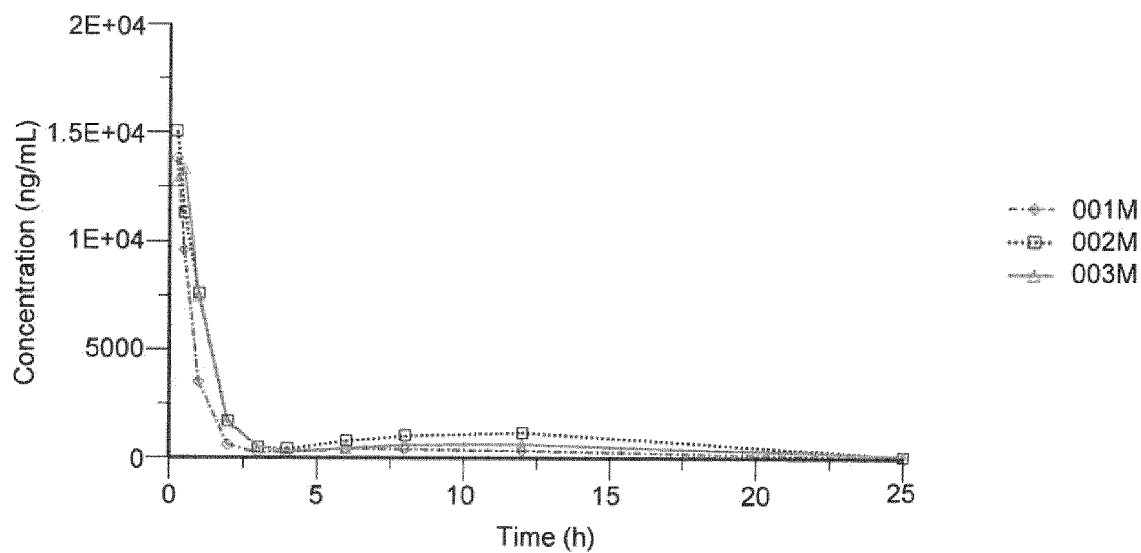
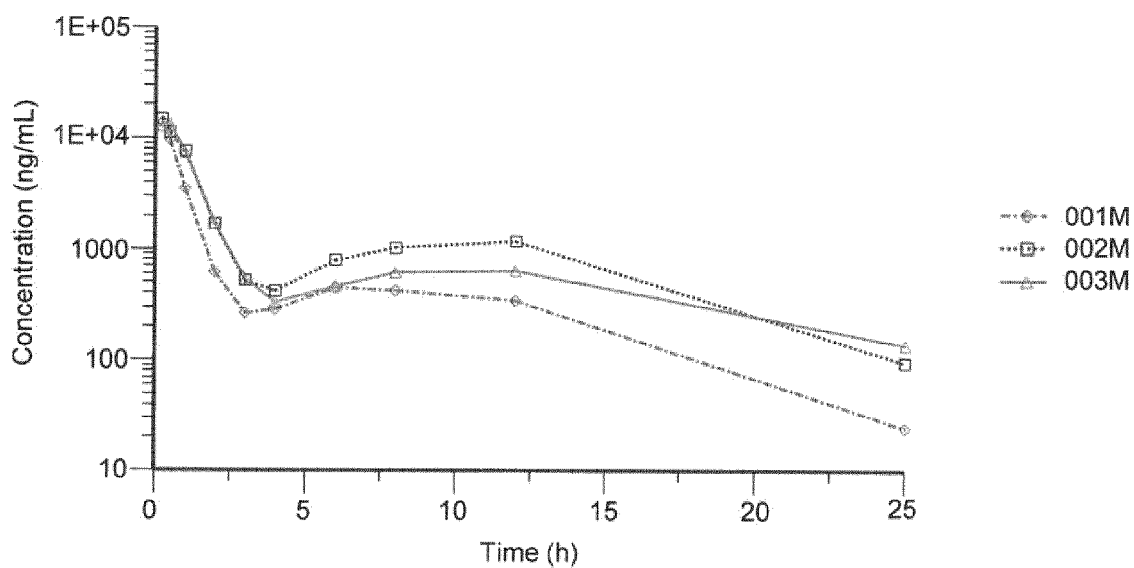
Fig. 15

COMPOUNDS FOR USE IN THE TREATMENT OR PROPHYLAXIS OF PAIN, INFLAMMATION AND/OR AUTOIMMUNITY

CROSS-REFERENCE TO RELATED APPLICATIONS

This application is a 371 filing of International Patent Application PCT/EP2020/051528 filed Jan. 22, 2020, which claims the benefit of European patent application no. 19153315.7 filed Jan. 23, 2019.

TECHNICAL FIELD

The present invention relates to a polymorphic form of (S,S)-2-N(3-O-(propan-2-ol)-1-propyl-4-hydroxybenzene)-3-phenylpropylamide or synonymously named N-[2-(4-Hydroxy-phenyl)-1-(2-hydroxy-propoxymethyl)-ethyl]-3-phenyl-propionamide and to the treatment or prophylaxis of pain, inflammation and/or autoimmunity and provides a method of treating or preventing pain, inflammation and/or autoimmunity as well as the use of this polymorphic form in the manufacture of medicaments for the treatment or prophylaxis of pain (preferably nociceptive or neuropathic), inflammation and/or autoimmunity in humans and/or non-human animals.

BACKGROUND

The compound 2-N(3-O-(propan-2-ol)-1-propyl-4-hydroxybenzene)-3-phenylpropylamide has been disclosed in U.S. Pat. No. 7,754,771 and its use in the treatment or prophylaxis of pain and inflammation has been described in WO 2009/1099850, WO 2011/030105, US 2011/0086910 and WO 2013/084238. Previous disclosures on this compound have related to the racemate containing all four enantiomers and diastereomers, namely (S,S), (S,R), (R,R) and (R,S). WO 2013/084238 mentioned that the racemate containing the S enantiomers at the chiral position adjacent to the amide exhibited particularly advantageous properties.

Pain is a multifaceted or multidimensional, experiential response to a variety of stimulus conditions. Pain is defined by the International Association for the Study of Pain (IASP) as "an unpleasant sensory and emotional experience associated with actual or potential tissue damage, or described in terms of such damage".

Pain in animals is frequently the result of nociception, i.e., activity in the nervous system that results from the stimulation of nociceptors. Neuropathic pain differs from nociceptive pain in that it involves damage to the nerve resulting in the sensation of pain. In central pain, the pain is generated in the brain from some form of lesion. Occasionally pain may be psychogenic, i.e., caused by mental illness.

Pain can be acute or chronic. Acute pain is usually caused by soft tissue damage, infection and/or inflammation among other causes. Acute pain serves to alert after an injury or malfunction of the body. Chronic pain may have no apparent cause or may be caused by a developing illness or imbalance. Chronic pain is defined as the disease of pain; its origin, duration, intensity and specific symptoms may vary.

The experience of physiological pain can be grouped according to the source and related nociceptors. Cutaneous pain is caused by injury to the skin or superficial tissues. Cutaneous nociceptors terminate just below the skin, and due to the high concentration of nerve endings, produce a well-defined, localised pain of short duration. Examples of injuries that produce cutaneous pain include paper cuts, minor cuts, minor (first-degree) burns and lacerations. Somatic pain originates from ligaments, tendons, bones, blood vessels and nerves. It is detected with somatic nociceptors. The scarcity of pain receptors in these areas produces a dull, poorly-localised pain of longer duration than cutaneous pain; examples include sprains and broken bones. Myofascial pain is usually caused by trigger points in muscles, tendons and fascia and may be local or referred. Visceral pain originates from the body's viscera or organs. Visceral nociceptors are located within body organs and internal cavities. The even greater scarcity of nociceptors in these areas produces pain that is usually more aching and for longer duration than somatic pain. Visceral pain is extremely difficult to localise, and several injuries to visceral tissue exhibit "referred" pain, where the sensation is localised to an area completely unrelated to the site of injury. Phantom limb pain, a type of referred pain, is the sensation of pain from a limb that has been lost or for which a person no longer receives physical signals. Neuropathic pain may occur as a result of injury or disease to the nerve tissue itself. This can disrupt the ability of the sensory nerves to transmit correct information to the thalamus, and hence the brain interprets painful stimuli even though there is no obvious psychological cause for the pain.

Acute pain is usually treated simultaneously with pharmaceuticals or appropriate techniques for removing the cause and pharmaceuticals or appropriate techniques for controlling the pain sensation, commonly analgesics.

Analgesics fall into three categories: opioid (narcotic) analgesics, non-opioid analgesics and adjuvant analgesics. Opioid analgesics are powerful analgesics that are chemically related to morphine. However, opioids have many side effects, which may be more likely to occur in people with certain disorders: kidney failure, a liver disorder, chronic obstructive pulmonary disease (COPD), dementia or another brain disorder. Drowsiness, constipation, nausea, vomiting and itching are common when opioids are started. Apart from morphine, opioid analgesics known at the time of writing include codeine, fentanyl, hydrocodone, hydromorphone, levorphanol, meperidine, methadone, oxycodone, oxymorphone, pentazocine and propoxyphene.

A variety of non-opioid analgesics are also available at the time of writing. They are often effective for mild to moderate pain. Most non-opioid analgesics are classified as non-steroidal anti-inflammatory drugs (NSAIDs). An example of an analgesic that is not an NSAID is acetaminophen, which is commonly known as paracetamol. Acetaminophen has substantially no anti-inflammatory properties.

NSAIDs are used to treat mild to moderate pain and may be combined with opioids to treat moderate to severe pain. NSAIDs not only relieve pain, but they also reduce the inflammation that often accompanies and worsens pain. Although widely used, NSAIDs can also have side effects, sometimes serious ones, including problems in the digestive tract, bleeding problems, problems related to retaining fluids and increased risk of heart and blood vessel disorders. Current NSAIDs include aspirin, ibuprofen, ketoprofen, naproxen, cox-2 inhibitors such as celecoxib, choline magnesium trisalicylate, diflunisal, salsalate, diclofenac, etodolac, fenoprofen, flurbiprofen, indomethacin, ketorolac, meclofenamate, mefenamic acid, meloxicam, nabumetone, oxaprozin, piroxicam, sulindac and tolmetin.

Adjuvant analgesics include antidepressants such, for example, as imipramine, amitriptyline, bupropion, desipramine, fluoxetine and venlafaxine; anticonvulsants (such as carbamazepine, gabapentin and pregabalin) and oral and topical local anaesthetics.

In the treatment of chronic pain, the "Three-Step Analgesic Ladder" developed by the World Health Organization is often used. For mild pain, acetaminophen, aspirin or other NSAIDs may be employed. For mild to moderate pain, weak opioids such as codeine and dihydrocodeine are employed in combination with acetaminophen, aspirin or other NSAIDs. In the case of moderate to severe pain, strong opioids such as morphine, diamorphine, or fentanyl, hydromorphone, methadone, oxycodone or phenazocine may be administered in combination with acetaminophen, aspirin or other NSAIDs.

The currently available treatments for neuropathic pain have only low to moderate efficacy, and many patients are left without significant pain relief. The lack of adequate pain relief for millions of people with neuropathic pain, as well as for those with other types of pain, represents a great unmet medical need, this invention addresses that need.

SUMMARY OF THE INVENTION

The present invention relates to a polymorphic form of (S,S)-2-N(3-O-(propan-2-ol)-1-propyl-4-hydroxybenzene)-3-phenylpropylamide and to the treatment or prophylaxis of pain, inflammation and/or autoimmunity and provides a method of treating or preventing pain, inflammation and/or autoimmunity as well as the use of this polymorphic form in the manufacture of medicaments for the treatment or prophylaxis of pain (preferably nociceptive or neuropathic), inflammation and/or autoimmunity in humans and/or non-human animals. More specifically, the compound used in the present invention is a compound of the following chemical formula:

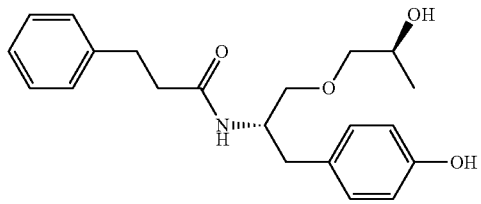 [SMILES: C[C@H](O)COC[C@H](Cc1ccc(O)cc1)NC(=O)CCc1ccccc1]

which is the (S,S)-isomer of 2-N(3-O-(propan-2-ol)-1-propyl-4-hydroxybenzene)-3-phenylpropylamide.

The present invention relates to a polymorph of this compound. A polymorph of this compound is used in the present invention. This polymorph, hereinafter also referred to as polymorph 2, can be characterized by methods such as X-ray, DSC and/or Raman spectroscopy.

Polymorph 2 has been surprisingly found to be less hygroscopic, more stable and more readily bioavailable than other crystal forms, such as polymorph 1, as discussed later.

DESCRIPTION OF FIGURES

FIG. 5 Analytical data sheet polymorph 1

FIG. 6 Analytical data sheet polymorph 2

FIG. 7 Predose bodyweights and calculated doses of NRD135S.E1 Form 1 (141232) and Form 2 (COEN4-091-M) following oral administration of NRD135S.E1 Form 1 (141232) and Form 2 (COEN4-091-M) to the male Beagle dog at a target dose level of 60 mg/kg FIG. 8 Actual Blood sampling Times Following Oral Administration of NRD135S.E1 Form 1 (141232) and Form 2 (COEN4-091-M) at a target dose level of 60 mg/kg on Week 2

FIG. 9 Mean and Individual Plasma concentrations of NRD135S.E1 Following Oral Administration of NRD135S.E1 Form 1 (141232) and Form 2 (COEN4-091-M) at a target dose level of 60 mg/kg FIG. 10 Mean and Individual Pharmacokinetic Parameters of NRD135S.E1 Form 1 (141232) and Form 2 (COEN4-091-M) in Male Beagle Dogs Plasma Following an Oral Administration at Nominal dose at 60 mg/kg on Week 1

FIG. 11 Mean and Individual Pharmacokinetic Parameters of NRD135S.E1 Form 1 (141232) and Form 2 (COEN4-091-M) in Male Beagle Dogs Plasma Following an Oral Administration of Nominal dose at 60 mg/kg on Week 2

FIG. 12 Following an Oral Administration at Nominal dose of 60 mg/kg Mean Plasma Concentrations of NRD135S.E1 Form 1 (141232) and Form 2 (COEN4-091-M) in Male Beagle Dogs FIG. 13 Individual Plasma Concentrations of NRD135S.E1 Form 1 (141232) in Male Beagle Dogs Following an Oral Administration of Nominal dose at 60 mg/kg (Sequence 1-1 Old)

FIG. 14 Individual Plasma Concentrations of NRD135S.E1 Form 2 (COEN4-091-M) in Male Beagle Dogs Following an Oral Administration of Nominal dose at 60 mg/kg (Sequence 2-1 New)

FIG. 15 Individual Plasma Concentrations of NRD135S.E1 Form 2 (COEN4-091-M) in Male Beagle Dogs Following an Oral Administration of Nominal dose at 60 mg/kg (Sequence 1-2 New)

DETAILED DESCRIPTION OF THE INVENTION

Figure 1:
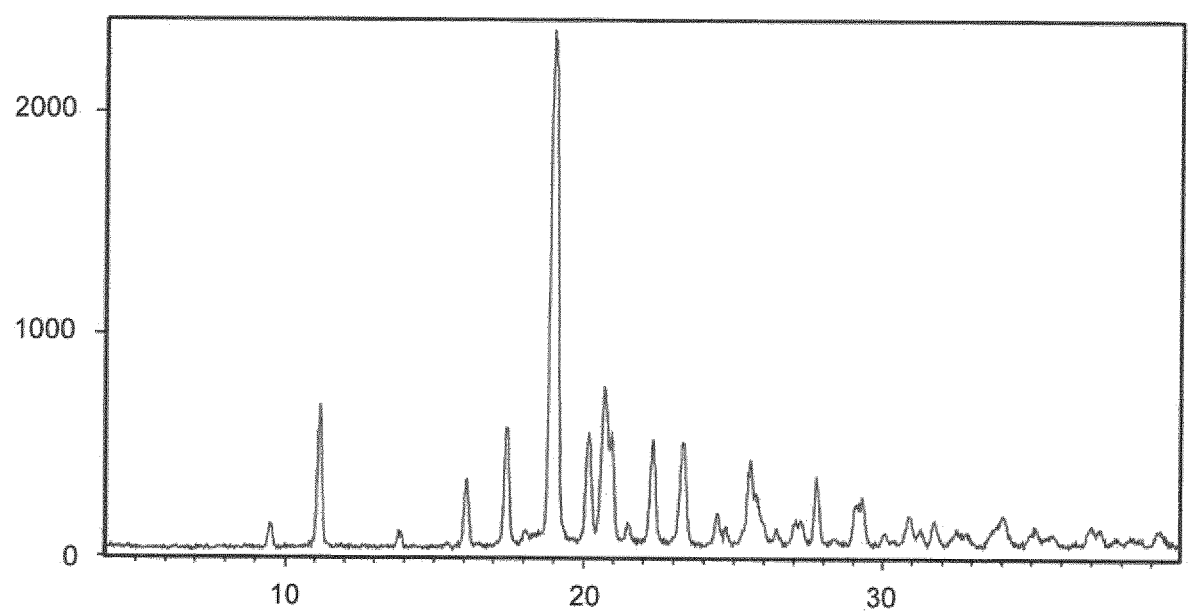
FIG. 1: X-ray powder diffraction pattern of polymorph 2

The present invention relates to a polymorphic form of a specific compound and to the treatment or prophylaxis of pain, inflammation and/or autoimmunity and provides a method of treating or preventing pain, inflammation and/or autoimmunity as well as the use of this polymorphic form in the manufacture of medicaments for the treatment or prophylaxis of pain (preferably nociceptive or neuropathic), inflammation and/or autoimmunity in humans and/or non-human animals. More specifically, the compound used in the present invention is a compound of the following chemical formula:

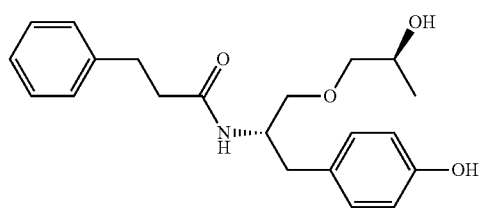

This compound ((S,S)-2-N(3-O-(propan-2-ol)-1-propyl-4-hydroxybenzene)-3-phenylpropylamide), including its enantiomers and diastereomers may be prepared as described in WO 2013/084238, which is incorporated herein by reference, particularly Examples 1 and 2 thereof.

The ((S,S)-2-N(3-O-(propan-2-ol)-1-propyl-4-hydroxybenzene)-3-phenylpropylamide) used in the present invention is an enantiomer that is preferably substantially free of other stereoisomeric forms of this compound. A representative substantially pure enantiomer comprises greater than 90% by weight of one enantiomer of the compound and less than 10% by weight of the other stereoisomeric forms of the compound, preferably greater than 95% by weight of one enantiomer of the compound and less than 5% by weight of the other stereoisomeric forms of the compound, even more preferably greater than 98% by weight of one enantiomeric form of the compound and less than 2% by weight of the other stereoisomeric forms of the compound. The term "other stereoisomeric forms" typically refers to the (S,R), (R,S) and (R,R) enantiomeric or diastereomeric forms of the compound 2-N(3-O-(propan-2-ol)-1-propyl-4-hydroxybenzene)-3-phenylpropylamide. The substantially pure (S,S)-enantiomer is capable of activating BLK and LynA tyrosine kinases, while it has no or substantially no effect on the activity of LynB tyrosine kinase A polymorph of this compound is used in the present invention. This polymorph, hereinafter also referred to polymorph 2, may be characterized by methods such as X-ray, DSC and/or Raman spectroscopy.

The present inventors have surprisingly found polymorph 2 to be less hygroscopic and more stable than other crystal forms, such as polymorph 1 as discussed later. Moreover, polymorph 2 was surprisingly found to have a better bioavailability as compared to polymorph 1. This is particularly surprising in view of its higher stability. Thermal analysis of polymorph 2 shows a melting point with an onset at 104.5° C. and a melting point peak at 107.2° C. The melting enthalpy $\Delta H_{melt}$ was about 121 J/g.

The thermal analysis for determining the melting point and melting enthalpy of the claimed polymorph may be conducted using a TGA/DTA analyzer (such as Perkin-Elmer STA 600 TGA/DTA analyzer) at 25° C. temperature, heating the sample at a rate of 10° C./min, typically from 25° C. to 300° C., during which time the change in weight is monitored as well as the differential thermal analysis (DTA) signal, while the purge gas used is nitrogen at a flow rate of 20 cm$^3$/min.

Scanning electron Microscopy (SEM) indicates that polymorph 2 has a regular rectangular block habit with particles ranging in size from 2 to 10 μm long and 2 to 5 μm wide. The particle size is typically expressed as the $D_{50}$ volume median particle diameter as measured using laser diffraction.

Gravimetric Vapour Sorption (GVS) shows that polymorph 2 is only slightly hygroscopic with a 0.6% weight gain to 80% RH.

Polymorph 2 of the invention may be isolated by preparing a slurry in water and crystallizing from a 50/50 mixture by weight of methanol and water. It may also be prepared by rapid cooling of a solution in chloroform and isopropyl acetate.

Polymorph 2 of the invention typically has an X-ray powder diffraction pattern (CuKα) comprising a peak at 19.0±0.2 °2θ, more preferably 19.0±0.1 °2θ and even more preferably 19.0±0.05 °2θ. More preferably, the polymorphic form has an X-ray powder diffraction pattern (CuKα) further comprising one or more peaks selected from peaks at 11.25±0.2, 17.38±0.2, 17.57±0.2, 20.74±0.2, 20.91±0.2, 22.42±0.2 and 23.30±0.2 °2θ. The further peaks are even more preferably selected from 11.25±0.1, 17.38±0.1, 17.57±0.1, 20.74±0.1, 20.91±0.1, 22.42±0.1 and 23.30±0.1 °2θ. Still more preferably, the peaks are selected from 11.25±0.05, 17.38±0.05, 17.57±0.05, 20.74±0.05, 20.91±0.05, 22.42±0.05 and 23.30±0.05 °2θ. Preferably, the peak at 19.0±0.2 °2θ, more preferably, at 19.0±0.1 °2θ, is the peak with the highest relative intensity in the X-ray powder diffraction pattern (CuKα) of polymorph 2 (in particular within the range of 5 to 40 °2θ).

Polymorph 2 preferably does not contain any peaks within the ranges of 15±0.3 °2θ and 16.5±0.2 °2θ. More preferably, polymorph 2 does not contain any peaks within the ranges of 15±0.5 °2θ and 16.5±0.3 °2θ.

Even more preferably, the X-ray powder diffraction pattern (CuKα) of Polymorph 2 of the invention is substantially as shown in FIG. 1.

Polymorph 2 typically melting point in the range from about 105° C. to about 110° C. More preferably, the melting point is in the range from about 106° C. to about 109° C., preferably about 107° C. to about 108° C.

In addition to the above, it has even more surprisingly been found in dog bioavailability tests, as described in the experimental data described herein, that the bioavailability of polymorph 2 of the invention is exceptionally high, and in particular higher than the bioavailability of polymorph 1.

In contrast, the characteristics of polymorph 1 indicate a higher hygroscopicity and lower stability than the inventive polymorph 2.

Namely, thermal analysis of polymorph 1 shows a melting point with an onset at 119.6° C. and a melting point peak at 125.6° C. The melting enthalpy $\Delta H_{melt}$ was about 19 J/g.

Simultaneous Thermal analysis (STA) data of polymorph 1 further indicates a small weight loss of just under 1% between 90 and 115° C. followed by the melt with onset at ~ 119.5° C. in a single thermal event. Polymorph 1 may thus be a partial hydrate.

Scanning electron Microscopy (SEM) indicates that polymorph 1 has mostly irregular shaped particles less than 10 μm across wide.

Gravimetric Vapour Sorption (GVS) shows that polymorph 1 is hygroscopic with a weight increase of ~ 1.3% to 70% RH. However, a rapid moisture uptake then follows between 70% and 80% RH to 5.6% and there is hysteresis (gap) between the adsorption and desorption cycles which hinted towards form change. This different form appeared to be more hygroscopic, with a second adsorption cycle showing a weight increase well above a satisfactory limit of 2% at an RH of just 40%.

Polymorph 1 may be prepared by recrystallizing from a variety of solvents, such as methanol, ethanol, 2-propanol, acetonitrile, acetone, 1,4-dioxane and dimethyl formamide.

Medical Uses

The present invention also relates to polymorph 2 for use as a medicament and to polymorph 2 for use in the treatment or prophylaxis of a disease selected from pain, inflammation and autoimmunity. The disease is preferably pain.

In addition, a pharmaceutical composition for use in the treatment or prophylaxis of pain, inflammation and/or autoimmunity is encompassed by the present invention, wherein the composition comprises a pharmaceutically effective amount of polymorph 2, optionally together with one or more pharmaceutically acceptable excipients. The pharmaceutical composition of the invention is additionally or alternatively provided for use in the treatment or prophylaxis of inflammation.

The pharmaceutical composition is preferably formulated as a unit dosage form. The unit dosage form preferably comprises from 0.1 to about 500 mg of polymorph 2.

The polymorph of the present invention may be used for the treatment or prophylaxis of acute or chronic pain. For instance, the polymorph may be used for the treatment of nociceptive pain such, for example, as cutaneous pain, somatic pain, myofascial pain, visceral pain, phantom limb pain or neuropathic pain. The polymorph of the invention may also be used in the treatment of headaches or migraine. The polymorph may be used alone or in combination with acetaminophen or another NSAID for the treatment of mild chronic pain or in conjunction with weak or strong opioids for the treatment of moderate or severe pain.

The polymorph of the invention may also be employed in the treatment or prophylaxis of neuropathic pain and may be used in conjunction with one or more antidepressants or antiepileptic medicaments such, for example, as gabapentin or pregabalin. According to another aspect of the present invention therefore there is provided a method for treating or preventing pain, inflammation and/or autoimmunity in a human or non-human animal patient, which method comprises administering to said patient in need thereof a therapeutic effective amount of the polymorph of the invention. For a human patient, a daily dose of 1.0 mg to 15 g of said polymorph in a pure, substantially pure or partially pure form as described in more detail below may suitably be administered. The polymorph may be administered under the supervision of a medical practitioner in an amount sufficient to achieve effective pain management. In some embodiments, the daily dose of said polymorph may be titrated to determine such effective amount. Said daily dose may comprise about 5.0 mg to 1 g, typically about 5 mg to 500 mg. In some embodiments, said dose may comprise 10 mg to 100 mg per day of the polymorph. The polymorph may be administered on a regimen of one to four times per day. Said polymorph may be administered parenterally, transdermally, intramuscularly, intravenously, intradermally, intranasally, subcutaneously, intraperitoneally, intraventricularly, intrathecally or rectally. Preferably, the polymorph is administered orally. Optionally, the polymorph of the present invention may be administered simultaneously, sequentially or separately with at least one opioid analgesic, an antidepressant or an antiepileptic medicament. Alternatively, the polymorph of the invention may be administered simultaneously, sequentially or separately with one or more other NSAIDs or acetaminophen.

The polymorph of the present invention may be used for the treatment or prophylaxis of autoimmunity, i.e. autoimmune diseases. In a preferred embodiment of the invention, the autoimmune disease is celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), dermatomyositis (DM) or multiple sclerosis (MS).

The present invention also relates to the use of the polymorph of the invention in the manufacture of a medicament for use in the treatment or prophylaxis of pain, inflammation and/or autoimmunity. Said medicament may be manufactured for coadministration with one or more of acetaminophen, another NSAID, an opioid, an antiepileptic or an antidepressant. In another embodiment, the invention provides for the use of the polymorph of the invention in the manufacture of a medicament for use in the treatment or inflammation of inflammation.

Advantageously, it has been found that the polymorph of the present invention is effective for reducing or preventing inflammation. It has also been found that the polymorph of the invention has no or substantially no (i.e., within acceptable limits) deleterious effect on the central nervous system.

In yet another aspect of the present invention there is provided a pharmaceutical composition for use in the treatment or prophylaxis of pain, inflammation and/or autoimmunity, said composition comprising a pharmaceutically effective amount of the polymorph of the invention. Said composition may further comprise one or more pharmaceutically acceptable excipients. In some embodiments, said composition may also comprise acetaminophen, one or more other NSAIDs, one or more weak or strong opioids, an antidepressant or an antiepileptic agent.

The pharmaceutical composition of the invention may comprise the polymorph of the invention in a pure, substantially pure or partially pure form. In some embodiments, said substantially pure form may comprise at least 95% wt. of said polymorph, e.g., 96% wt., 97% wt., 98% wt. or more than 99% wt. of said polymorph.

The composition may be formulated as a tablet, a pill, a capsule, a powder, granules, a sterile parenteral solution or suspension, a metered aerosol or liquid spray, drops, an ampoule, an auto-injector device, a suppository, a cream or a gel. Said composition may be adapted for oral, enteral parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said polymorph may be mixed with one or more pharmaceutical excipients, e.g., conventional tabletting ingredients such as corn starch, lactose, sucrose, sorbitol, talc, stearic acid, magnesium stearate, dicalcium phosphate or gums, or other pharmaceutical diluents, e.g., water, to form a solid pre-formulation composition containing a substantially homogeneous mixture of said polymorph, such that said polymorph is dispersed evenly throughout the composition, so that the composition may be readily subdivided into equally effective unit dosage forms such as tablets, pills and capsules.

Said solid pre-formulation composition is then subdivided into unit dosage forms of the kind mentioned above which may each contain from 0.1 to about 500 mg of the polymorph of the present invention. Favoured unit dosage forms contain from 1 to 500 mg, e.g., 1, 5, 10, 25, 50, 100, 300 or 500 mg, of the polymorph of the present invention.

When formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

Alternatively, the pharmaceutical composition of the present invention may be formulated as a liquid dosage form for administration orally or by injection; for example an aqueous solution, a suitably flavoured syrup, an aqueous or oil suspension or a flavoured emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinylpyrrolidone or gelatin.

In addition, the present invention also relates to a method for treating or preventing pain, inflammation and/or autoimmunity in a human or non-human animal patient in need thereof, wherein the method comprises administering to said patient a therapeutic effective amount of polymorph 2 or the pharmaceutical composition containing polymorph 2. In this method, a daily dose of 0.1 mg to 15 g of polymorph 2 is administered. Polymorph 2 is preferably administered orally.

The following definitions apply throughout the present specification, unless specifically indicated otherwise.

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (e.g. disease modifying, preferably leading to a complete response and eventually to healing of the disorder or disease) and palliative treatment (including symptomatic relief).

The term "prevention" or "prophylaxis" of a disorder or disease as used herein is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" or "prophylaxis" comprises the use of the polymorph of the present invention before any clinical and/or pathological symptoms are diagnosed or determined or can be diagnosed or determined by the attending physician.

The term "about" preferably refers to ±10% of the indicated numerical value, more preferably to ±5% of the indicated numerical value, and in particular to the exact numerical value indicated. For example, the expression "about 100" preferably refers to 100±10% (i.e., 90 to 110), more preferably to 100±5% (i.e., 95 to 105), and even more preferably to the specific value of 100. If the term "about" is used in connection with the endpoints of a range, it preferably refers to the range from the lower endpoint 10% of its indicated numerical value to the upper endpoint+10% of its indicated numerical value, more preferably to the range from of the lower endpoint 5% to the upper endpoint+5%, and even more preferably to the range defined by the exact numerical values of the lower endpoint and the upper endpoint. Thus, the expression "about 10 to about 20" preferably refers to the range of 9 to 22, more preferably to the range of 9.5 to 21, and even more preferably to the range of 10 to 20. If the term "about" is used in connection with the endpoint of an open-ended range, it preferably refers to the corresponding range starting from the lower endpoint 10% or from the upper endpoint+10%, more preferably to the range starting from the lower endpoint 5% or from the upper endpoint+5%, and even more preferably to the open-ended range defined by the exact numerical value of the corresponding endpoint. For example, the expression "at least about 10%" preferably refers to at least 9%, more preferably to at least 9.5%, and even more preferably to at least 10%.

The terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, if a component of a composition is indicated to be "optional", the invention specifically relates to both possibilities, i.e., that the corresponding component is present (contained in the composition) or that the corresponding component is absent from the composition.

The term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

Any parameters referred to herein (including, e.g., any amounts/concentrations indicated in "mg/ml" or in "% (v/v)", and any pH values) are preferably to be determined at standard ambient temperature and pressure conditions, particularly at a temperature of 25° C. (298.15 K) and at an absolute pressure of 1 atm (101.325 kPa).

It is to be understood that the present invention specifically relates to each and every combination of features and embodiments described herein, including any combination of general and/or preferred features/embodiments.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXAMPLES

Examples of the present invention are given purely for illustrative and non-limiting purposes.

Example 1—Preparation of (S,S)-2-N(3-O-(propan-2-ol)-1-propyl-4-hydroxybenzene)-3-phenylpropylamide (S,S)-2-N(3-O-(propan-2-ol)-1-propyl-4-hydroxybenzene)-3-phenylpropylamide was prepared as described in WO 2013/084238 and US 2011/0086910.

In a first step, 2 g of methyl lactate was reacted with excess of benzyl bromide to get 880 mg of (S)-benzyloxymethyl lactate. The reaction was performed by slurring sodium hydride in THF and cooling down to approximately −15° C. The reaction mixture was then allowed to warm slowly to room temperature and stirred for approximately 1 to 2 hours. The reaction was quenched with saturated ammonium chloride solution and extracted with MTBE twice followed by the removal of solvent on a rotary evaporator to obtain a crude oil. The crude product was purified by column chromatography to yield pure (S)-2-benzyloxymethyl lactate. The (R)-2-benzyloxymethyl lactate isomer was present at 0.93% only. The yield of this step may be increased by avoiding the presence of moisture in the reaction solution.

In a second step, 880 mg (S)-2-benzyloxymethyl lactate obtained in step 1 were reduced using lithium aluminum hydride to obtain (S)-2-benzyloxypropylene glycol in 83.8% yield with 98.7% purity. A solution of pure (S)-2-benzyloxymethyl lactate in methylene chloride was stirred and a solution of lithium aluminum hydride was slowly added thereto at approximately 5° C. The reaction was monitored by TLC and quenched by USP-PW water very carefully. No racemization occurred in this step.

In a third step, the (S)-2-benzyloxypropylene glycol was then reacted with methane sulfonyl chloride in methylene chloride in the presence of triethyl amine to yield the mesylate in 88% yield. A solution of step 2 was stirred in methylene chloride and methane sulfonyl chloride was added to it dropwise at <5° C. After the addition was complete, the progress of the reaction was monitored by TLC. The reaction was quenched with USP-PW water. After the layers were separated, the aqueous layer was back extracted with methylene chloride. The methylene chloride layers were then combined and washed with USP-PW water 3 times to remove most of the methane sulfonic acid. No racemization occurred in this step.

In a fourth step, the mesylate (of step 3) was coupled with S—O-benzyl tyrosinol to form the bis-protected product in 22.7% yield, with a purity of 97.4%. The reaction was carried out at room temperature using a combination of DMF as the solvent and sodium hydride as the base. The reaction went to completion after stirring for at least 12 hours at room temperature.

In a fifth step, 340 mg of the product of step 4 were reduced by hydrogenation in the presence of 10% palladium on carbon catalyst and hydrochloric acid using methylene chloride as a solvent at 50° C. The reaction went to completion in approximately 4 hours with no racemization to yield the desired product in 84.3% yield and 98.9% purity. More specifically, the catalyst was removed by filtration and the filtrate was then concentrated at 33° C. The resulting mixture of solid and oil was mixed with ethyl acetate. The resulting slurry was filtered and the solids washed with ethyl acetate and dried under vacuum at 40 to 45° C. to obtain the desired product.

Example 2—Preparation of Polymorph 2

(S,S)-2-N(3-O-(propan-2-ol)-1-propyl-4-hydroxybenzene)-3-phenylpropylamide (500 mg) was suspended in water (5 mL) and the resulting suspension was shaken and temperature-cycled between 40° C. and 25° C. every 4 hours for 72 hours. Excess water was decanted off as far as practicably possible using a syringe and needle. Thereafter, the product was dried, initially by evaporation of the water at ambient temperature then at 50° C. under vacuum until a constant weight was achieved.

Method Use for Analysis of the Polymorphs
X-Ray Powder Diffraction (XRPD)

Approximately 5 mg of sample was gently compressed on the XRPD zero back ground single obliquely cut silica sample holder. The sample was then loaded into a Philips X-Pert MPD diffractometer and analysed using the following experimental conditions.

Tube anode: Cu
Generator tension: 40 kV
Tube current: 40 mA
Wavelength alpha1: 1.5406 Å
Wavelength alpha2: 1.5444 Å
Start angle [2 theta]: 5
End angle [2 theta]: 50
Continuous scan Representative X-ray data was acquired at a slower scan speed over a range of 4–40°2θ.

Raman Spectroscopy
Raman

Raman spectra were acquired on a Bruker RFS 100/S utilizing excitation wavelength of 1064 nm. The samples were prepared for analysis by placing the material in a sample holder and positioning this in the spectrometer.

Simultaneous Thermal Analysis (STA)

Simultaneous thermal analysis (STA) in this context refers to the simultaneous application of thermogravimetry (TGA) and differential thermal analysis (DTA) to one and the same sample in a single instrument.

Approximately 5 mg of sample was accurately weighed into a ceramic crucible and it was placed into the chamber of Perkin-Elmer STA 600 TGA/DTA analyzer at ambient (25° C.) temperature. The sample was then heated at a rate of 10° C./min, typically from 25° C. to 300° C., during which time the change in weight was monitored as well as DTA signal. The purge gas used was nitrogen at a flow rate of 20 cm³/min.

Differential Scanning Calorimetry (DSC)

DSC was investigated with a Netzsch-DSC 204 F1 Phoenix. Approximately 5-6 mg of the sample was placed into a DSC pan. The analysis was performed in a sealed aluminum pan with a pinhole. The sample was heated under nitrogen atmosphere from 25 to 125° C. at a rate of 10 K/min.

Scanning Electron Microscopy (SEM) Scanning Electron Microscopy was performed using a Tescan Vega3 Scanning Electron Microscope operating at 15 KV and a slight tilt of 15°.

Prior to analysis samples were prepared by adhering the sample to an SEM stub using double sided carbon impregnated sticky tabs supplied by Agar Scientific.

The prepared stubs were then coated with 15 nm gold using a Quorum Q150ES sputter coater.

Gravimetric Vapour Sorption (GVS)

Approximately 10 mg of sample was placed into a wire-mesh vapour sorption balance pan and loaded into an 'IgaSorp' vapour sorption balance (Hiden Analytical Instruments). The sample was then dried by maintaining a 0% humidity environment until no further weight change was recorded. Subsequently, the sample was subjected to a ramping profile from 0-90% RH at 10% RH increments, maintaining the sample at each step until equilibration had been attained (99% step completion). Upon reaching equilibration, the % RH within the apparatus was ramped to the next step and the equilibration procedure repeated. After completion of the sorption cycle, the sample was then dried using the same procedure. The weight change during the sorption/desorption cycles were then monitored, allowing for the hygroscopic nature of the sample to be determined.

Results of the Analysis of the Polymorphs

The XRPD obtained was as shown in FIG. 1. In the following, a listing of the observed peaks is provided.

TABLE 1

| Position [°2θ] | Height [cts] | FWHM Left [°2θ] | d-spacing [Å] | Relative Intensity [%] |
|---|---|---|---|---|
| 7.8142 | 64.76 | 0.2342 | 11.31424 | 1.77 |
| 9.5751 | 148.88 | 0.1004 | 9.23703 | 4.06 |
| 11.0922 | 494.90 | 0.1171 | 7.97688 | 13.49 |
| 11.2534 | 729.20 | 0.1171 | 7.86298 | 19.88 |
| 13.8655 | 94.91 | 0.2007 | 6.38697 | 2.59 |
| 16.1232 | 400.23 | 0.1673 | 5.49737 | 10.91 |
| 17.3820 | 830.84 | 0.1004 | 5.10197 | 22.65 |
| 17.5766 | 705.98 | 0.1004 | 5.04592 | 19.24 |
| 18.0595 | 115.54 | 0.1673 | 4.91207 | 3.15 |
| 19.0182 | 3668.47 | 0.1840 | 4.66658 | 100.00 |
| 20.1171 | 642.72 | 0.1171 | 4.41407 | 17.52 |
| 20.7352 | 1113.40 | 0.1338 | 4.28387 | 30.35 |
| 20.9093 | 1063.71 | 0.2676 | 4.24859 | 29.00 |
| 21.5697 | 321.51 | 0.1673 | 4.11997 | 8.76 |
| 22.2235 | 624.43 | 0.1338 | 4.00023 | 17.02 |
| 22.4170 | 690.54 | 0.1338 | 3.96613 | 18.82 |
| 23.3016 | 816.32 | 0.3011 | 3.81753 | 22.25 |
| 24.4333 | 232.43 | 0.1338 | 3.64321 | 6.34 |
| 25.5555 | 658.66 | 0.2342 | 3.48572 | 17.95 |
| 26.0885 | 221.55 | 0.1004 | 3.41571 | 6.04 |
| 26.5053 | 161.46 | 0.2007 | 3.36294 | 4.40 |
| 26.9953 | 190.19 | 0.1338 | 3.30299 | 5.18 |
| 27.3243 | 244.20 | 0.2342 | 3.26397 | 6.66 |
| 27.7554 | 485.75 | 0.1338 | 3.21458 | 13.24 |
| 27.9287 | 392.11 | 0.1004 | 3.19470 | 10.69 |
| 28.4146 | 111.14 | 0.2676 | 3.14115 | 3.03 |
| 29.0727 | 481.13 | 0.1004 | 3.07154 | 13.12 |
| 29.3470 | 502.21 | 0.1673 | 3.04345 | 13.69 |
| 30.1336 | 141.80 | 0.2676 | 2.96577 | 3.87 |
| 30.8642 | 283.90 | 0.1673 | 2.89721 | 7.74 |
| 31.3612 | 180.65 | 0.1673 | 2.85243 | 4.92 |
| 31.8212 | 261.34 | 0.2342 | 2.81223 | 7.12 |
| 32.5372 | 211.67 | 0.2342 | 2.75197 | 5.77 |
| 32.8345 | 156.37 | 0.1673 | 2.72772 | 4.26 |
| 34.1862 | 251.13 | 0.2676 | 2.62290 | 6.85 |
| 35.0957 | 192.69 | 0.1673 | 2.55699 | 5.25 |
| 35.6799 | 147.37 | 0.1673 | 2.51645 | 4.02 |
| 36.9814 | 236.11 | 0.2007 | 2.43082 | 6.44 |
| 37.2854 | 169.91 | 0.2342 | 2.41170 | 4.63 |
| 37.8147 | 117.77 | 0.1338 | 2.37915 | 3.21 |
| 38.3576 | 129.23 | 0.2676 | 2.34672 | 3.52 |
| 39.2479 | 193.48 | 0.1338 | 2.29551 | 5.27 |

$^1$H-NMR spectra were measured for (S,S)-2-N(3-O-(propan-2-ol)-1-propyl-4-hydroxybenzene)-3-phenylpropylamide before and after crystallization to obtain polymorph 2. These spectra where consistent with each other, indicating that no chemical conversions had occurred.

Figure 4:
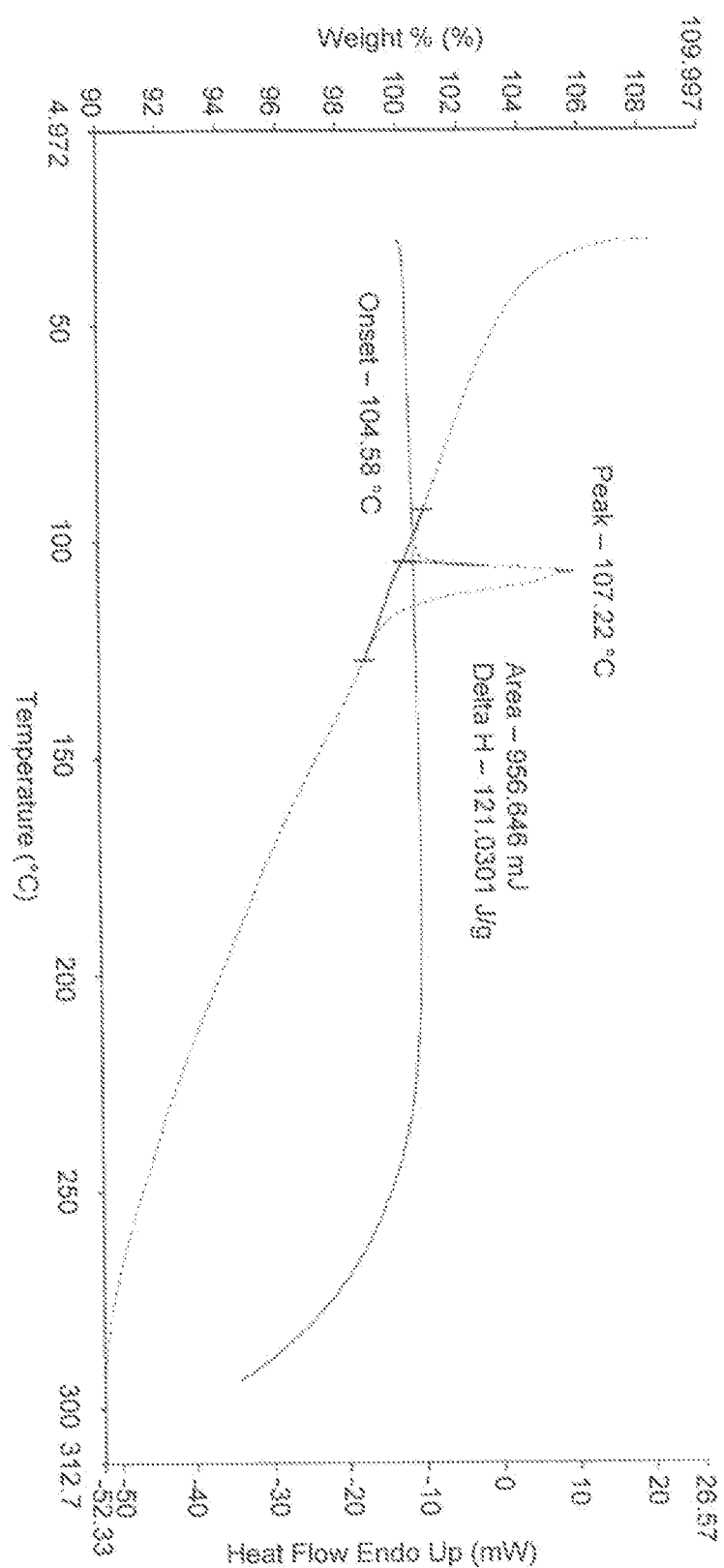
FIG. 4: TGA/DTA data of polymorph 2
Figure 16:
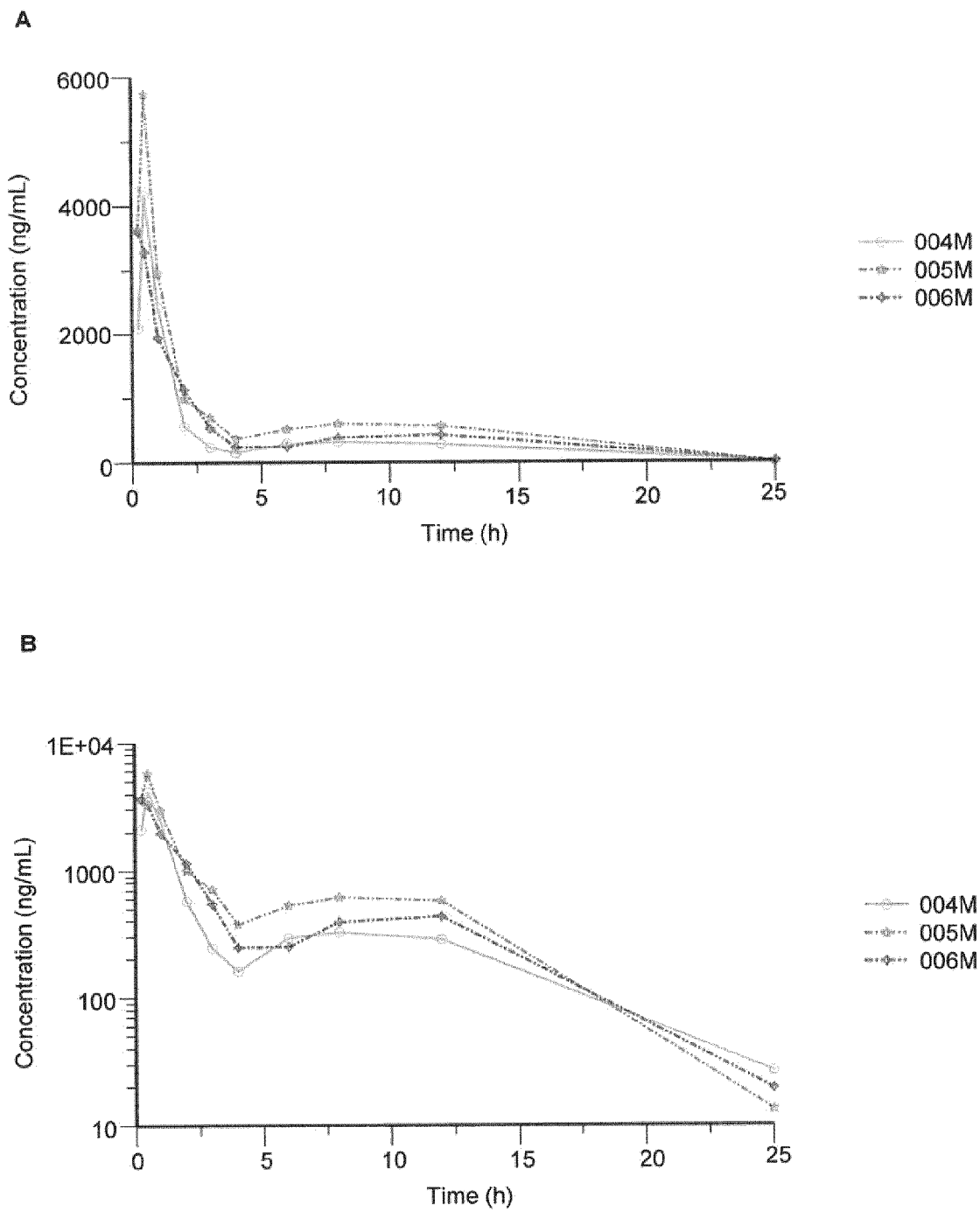
FIG. 16 Individual Plasma Concentrations of NRD135S.E1 Form 1 (141232) in Male Beagle Dogs Following an Oral Administration of Nominal dose at 60 mg/kg (Sequence 2-2 Old)
Figure 17:
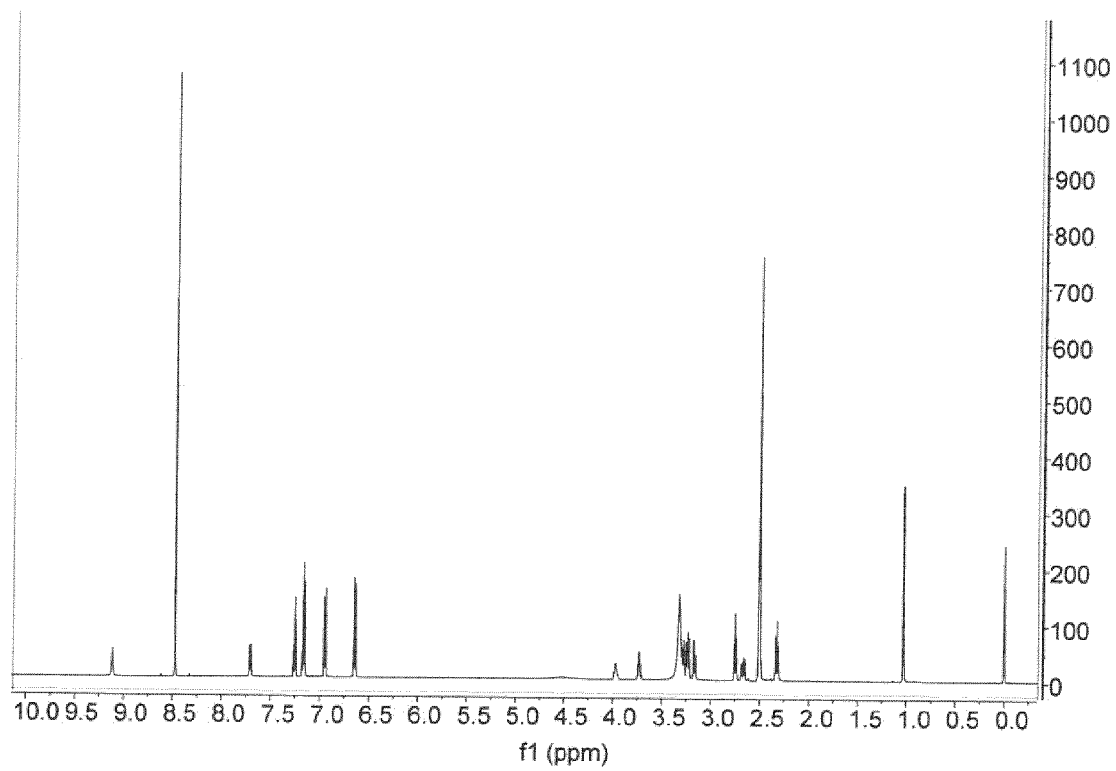
FIG. 17 $^1$H-NMR spectra for (S,S)-2-N(3-O-(propan-2-ol)-1-propyl-4-hydroxybenzene)-3-phenylpropylamide

The STA data showed no weight loss, which shows that the sample was not hydrated or solvated. The DTA thermogram (cf. FIG. 4) shows a sharp melt with onset at about 104.5° C.

Figure 2:
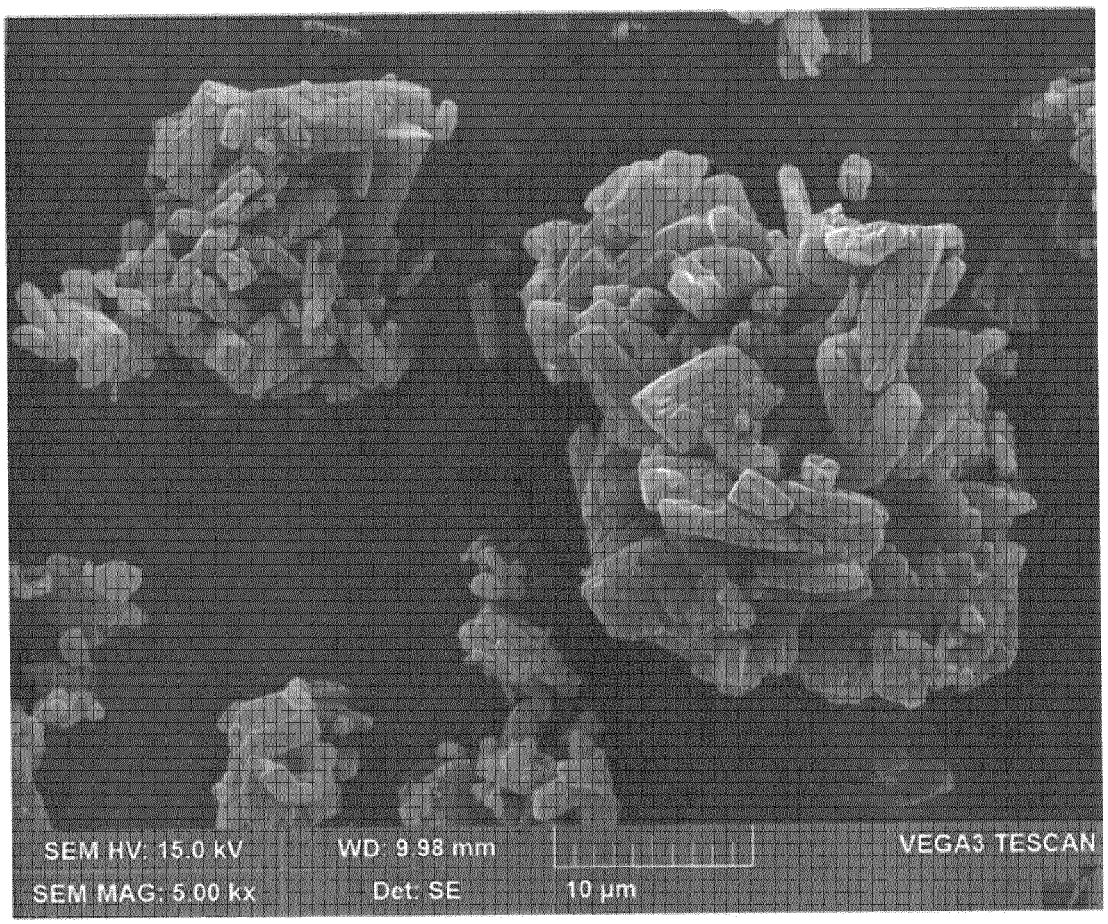
FIG. 2: SEM picture of polymorph 2
Figure 3:
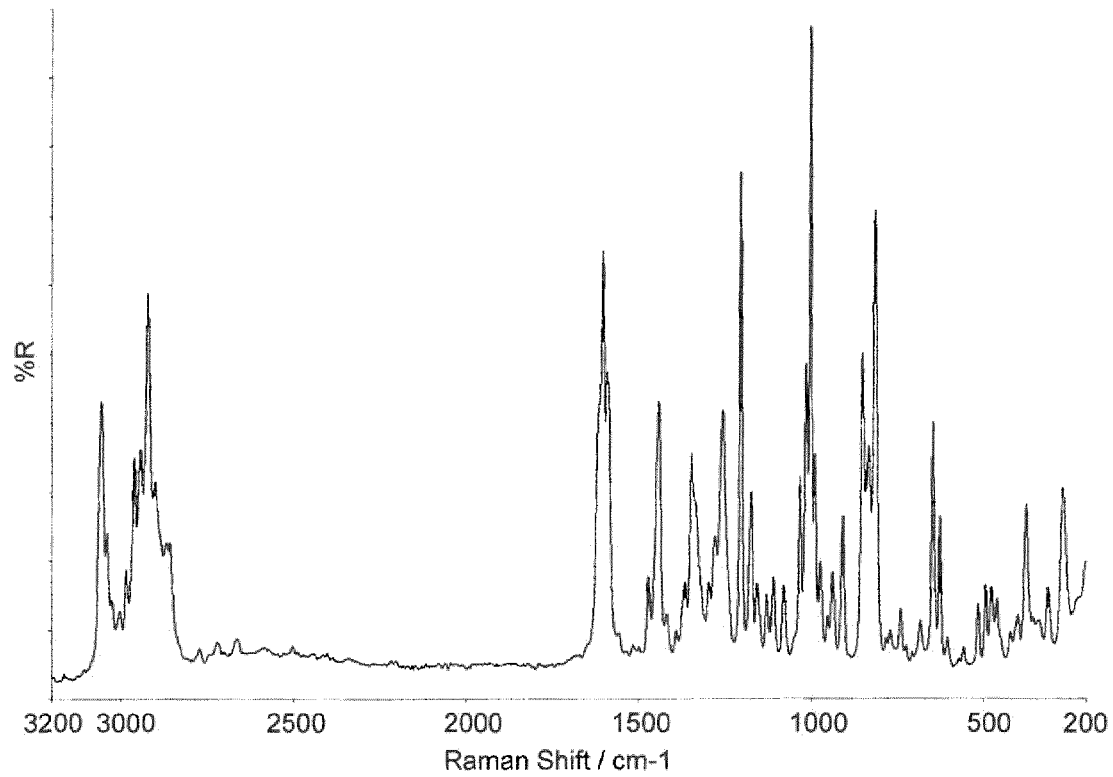
FIG. 3: Raman spectrum of polymorph 2, as measured on Bruker RFS 100/S at 1064 nm

Scanning electron Microscopy (SEM) (cf. FIG. 2) indicated this form had a regular rectangular block habit with particle diameters ranging from 2 to 10 μm length and 2 to 5 μm width.

GVS showed that the sample was only slightly hygroscopic with a 0.6% weight gain to 80% RH which indicates Form 2 was less hygroscopic than Form 1. There was a sharp weight loss at 90% RH for both cycles which may have been the result of further crystallisation of amorphous content. This resulted in an overall weight loss of ~ 1% by the end of the two adsorption/desorption cycles, but XRPD indicated no change of polymorphic form.

Example 3—Bioavailability of Polymorph 1 and 2

This study was designed to obtain blood plasma samples to enable the comparison of the bioavailability and pharmacokinetics of two different polymorphs 1 and 2 following single-dose oral administration to six dogs. A cross-over design was used with three dogs treated according to sequence 1 (polymorph 2 after 1) and three dogs according to sequence 2 (polymorph 1 after 2) with a one-week washout period between treatments.

Concentration-time profiles after both polymorphs were characterized by rapid absorption and a sharp concentration decline after peak concentrations; secondary humps in the profiles at 4 hours and beyond were suggestive of enterohepatic recirculation.

Measures of exposure to the drug, maximum observed concentration (Cmax) and area under the plasma concentration-time curve (AUC), appeared to be higher after polymorph 2 than after polymorph 1. The least squares (LS) geometric mean estimate for the AUC(0–∞) (corrected to a 60.0 mg dose) for polymorph 1 was 13170 h·ng/mL, for polymorph 2 20064 h·ng/mL (p=0.0016). The corresponding $C_{max}$ values (corrected to a 60.0-mg dose) were 4986 ng/mL (polymorph 1) and 11088 ng/mL (polymorph 2) (p=0.0009) respectively. Hence geometric mean ratios (polymorph 2/polymorph 1) of 1.52 (90% CI: 1.35, 1.71) for the AUC measure and of 2.22 (90% CI: 1.84; 2.70) for the Cmax measure resulted. The results and conclusions from the analyses were not different, if the respective parameters were not corrected for dose differences or if unextrapolated AUC values were analyzed. These differences between polymorphs show a higher availability of polymorph 2.

Polymorph 1 was supplied by Quay Pharmaceuticals as a white powder and was stored at ambient temperature at the Test Facility. A copy of the Analytical Data Sheet for NRD 135S.E1 Form 1 is presented in FIG. 5.

Polymorph 2 was prepared as detailed above. A copy of the Analytical Data Sheet for NRD 135S.E1 Form 1 is presented in FIG. 6.

Each polymorph was prepared as a suspension in a vehicle of 0.5% w/v HPMC K15M/0.5% w/v Tween 80 in sterile water.

Six male Beagle dogs (Tattoo numbers: 4986, 0964, 3611, 2380, 5002 and 1122 on-study animal numbers: 001 M, 002M, 003M, 004M, 005M and 006M, respectively) body-weight 9.5-11.5 kg, aged 2-7 years at dosing, currently held as part of a colony of animals (Colony number: 190431) were used on this study. Dogs were originally obtained from Marshall Farms USA Inc. (NY, USA) or Envigo RMS, and were bred for use in scientific procedures. During pre-trial and on-study periods, the animals were group-housed in caging appropriate to the species. Prior to acceptance for use on study, animals were subject to a veterinary examination and the results found to be satisfactory. Holding and study areas had automatic control of light cycles and temperature. Light hours were 0700-1900 h. Ranges of temperature and humidity measured during the study were 17.0-21.8° C. and 23.4-83.07%, respectively. All animals were weighed prior to each dose administration and the bodyweights recorded. With the exception of a period of fasting from overnight predose until 4 hours post dose, a daily allowance of 200-300 g of standard laboratory diet of known formulation (SDS D3 (E) SQC) was available. Mains quality tap water was available ad libitum.

The formulation was always prepared on the morning of dose administration. Each polymorph was prepared as a suspension at a concentration of 12 mg/mL in a vehicle of 0.5% w/v HPMC K15M/0.5% w/v Tween 80 in sterile water for injection. The required volume of vehicle was added to an appropriate formulation container.

The volume of vehicle required was calculated as follows:

$$V = (K \times D) \times 1.25$$

Where:
V=Final Volume
K=Number of kg to be dosed
D=Dose volume (mL/kg)
1.25=Formulation excess The required amount of test item was accurately weighed. Test items were weighed using the appropriate conversion factors and the following equation:

$$W = (C \times V \times 100)/P$$

Where:
W=Weight required (mg)
C=Target formulation concentration (mg/mL as free base)
V=Final Volume
P=Purity as free base (Polymorph 1=98.1% Polymorph 2=98.7%)

The test item was then added in small amounts (under magnetic stirring) into the same container as the dose vehicle. Formulations were then left under magnetic stirring for 15 minutes. An Ultraturrax homogeniser was used for 15 minutes at average speed to obtain a homogenous suspension. The formulation was then left under magnetic stirring until a homogenous suspension was achieved. The pH of the formulation was measured and the value recorded. If pH was below 3 this was adjusted to above level 3 with the addition of 1 M NaOH. On completion of formulation, 3×100 µL dose aliquots were taken. Dose aliquots and any remaining formulation were stored at −80° until shipment.

A summary of each formulation is presented in the table below:

TABLE 2

| Week | Sequence - Period Treatment | Material Batch ID | Wt. of Test Item (g) | Wt. of free base equivalent (g) | Vol. of vehicle (mL) | Wt. of formulation (g) | Con$^c$ (mg/g) | Visual appearance |
|---|---|---|---|---|---|---|---|---|
| 1 | 1-1 Old | 141232 | 2.85 | 2.80 | 237 | 233 | 12.0 | Fine, particulate homogenous suspension |
|   | 2-1 New | COEN4_091-M | 2.84 | 2.80 | 233 | 227 | 12.3 | Fine, milky white homogenous suspension |
| 2 | 1-2 New | COEN4-091-M | 2.85 | 2.80 | 237 | 227 | 12.8 | Fine, particulate homogenous suspension |
|   | 2-2 Old | 141232 | 2.84 | 2.80 | 233 | 219 | 12.3 | Fine, milky white homogenous suspension |

Each group of 3 male dogs, received a single oral dose administration of a polymorph at a target dose level of 60 mg/kg. Following a wash out period of 1 week each group of 3 male dogs received the alternative polymorph.

Animals were dosed according to the table below:

TABLE 3

| Week | Sequence - Period Treatment | Material Batch ID | Dose Route | Animal ID | Dose Level [1] (mg/kg) | Dose Concentration [1] (mg/mL) | Dose Volume (mL/kg) |
|---|---|---|---|---|---|---|---|
| 1 | 1-1 Old | 141232 | PO | 001M-003M | 60 | 12 | 5 |
|   | 2-1 New | COEN4_091-M |    | 004M-006M | 60 | 12 | 5 |
| 2 | 1-2 New | COEN4-091-M |    | 001M-003M | 60 | 12 | 5 |
|   | 2-2 Old | 141232 |    | 004M-006M | 60 | 12 | 5 |

[1] Target value

For each group, whole blood samples (ca 1.0 mL) were collected from the jugular veins in to NaF/EDTA tubes at the following time points:

Predose, 0.25, 0.5, 1, 2, 3, 4, 6, 8, 12 and 25 h post dose.

Times given above were target times which were adhered to as closely as possible. Actual times of sample collection (and of dosing) were recorded (Table 2) and used in the evaluation of pharmacokinetic parameters. Immediately following collection, blood samples were placed on wet ice. As soon as practically possible the blood samples were centrifuged (+4° C., 1500 g, 10 min). The resulting plasma was divided into two aliquots (vial A: 100 µl plasma, vial B: remaining volume) and stored in appropriately labelled polypropylene tubes in a freezer set to maintain a temperature of −80° C. until shipment. All plasma samples, remaining dose formulation and dose aliquots were stored in a freezer set to maintain a temperature of −80° C. until shipment.

Pharmacokinetic (PK) parameters were estimated using Phoenix pharmacokinetic software using a non-compartmental approach consistent with the oral route of administration. All parameters were generated from polymorph 1 and 2 individual concentrations in plasma. Parameters were estimated using nominal sampling times relative to the start of each dose administration within an allowable deviation range (±10%). Predose samples below the limit of quantification (0.5 ng/mL) were assumed to be 0 for the PK analysis.

The area under the polymorph 1 and 2 plasma concentration versus time curve (AUC) was calculated using the linear trapezoidal method with linear interpolation. The terminal elimination phase of each concentration versus time curve was identified by visual inspection of semilogarithmic concentration-time plots. Due to the irregularities in the profiles caused by the enterohepatic recirculation of drug in most cases only the last two observed concentration values could be used in this calculation. The slope of the terminal elimination phase was determined using log linear regression on unweighted concentration data. Parameters relying on the determination of the terminal elimination phase were not to be reported (NR) if the coefficient of determination was less than 0.800 and/or if the extrapolation of the AUC to infinity represented more than 20% of the total area. The parameters described in Text Table 1 were reported to 3 significant figures, with the exception of Tmax which has been reported to no more significant figures than needed to explain time. Additional parameters were automatically generated by Phoenix, which were not required by the Protocol, but are maintained in the raw data.

A statistical analysis of the relative bioavailability of the polymorphs was performed. The calculations were done in agreement with the FDA Guidance document: Statistical Approaches to Establishing Bioequivalence as follows:

Following natural logarithmic transformation, AUC(0–∞), AUC(0–t) and Cmax values without and with normalization for dose differences were subjected to linear mixed-effects model analysis procedures including terms for sequence, subject nested within sequence, period and treatment (polymorph). Additionally, the terminal elimination rate constant and its associated half-life, clearance (CL/F) and volume of distribution (V/F) were compared statistically using the same analysis modalities. All statistical analyses were performed using SAS© v9.4; the SAS code is provided in Appendix 3A while the procedure's output is provided in appendix 3B. The difference of the least squares means and their 90% CI of the NEW polymorph to OLD were estimated using the error variance obtained from the model. The point and interval estimates were back transformed to give estimates of the ratio of NEW relative to OLD geometric means. For Tmax, the median difference of 1 vs. 2 polymorph and its 90% CI were calculated.

All oral administrations of polymorph 1 and 2 were performed without incident. No adverse reactions to the oral administration were observed in any of the animals dosed. The body weights and dose administration details are presented in FIG. 7. All blood samples were collected on or close to (±6 min) target sampling times. Actual blood sampling times are presented in FIG. 8. Data generated from plasma samples collected at the Test Facility and subsequently shipped to the Sponsor's representative for bioanalysis was used to generate pharmacokinetic parameters of polymorph 1 and 2. The results of the plasma analysis of quality control samples gave assurance in the results reported for the study samples.

Individual plasma concentration results of forms 1 and 2 are presented in FIG. 9.

Mean and individual pharmacokinetic parameter results of forms 1 and 2 are presented in FIG. 10 and FIG. 11. Mean concentration versus time profiles following oral administration of forms 1 and 2 are presented in FIG. 12. Individual concentration versus time profiles of forms 1 and 2 are presented in FIGS. 13 to 16.

After thawing of the aliquots retained from the dosing formulation and from each individual final dosing suspension no homogeneous suspension could be obtained anymore so that no valid concentration results could be obtained from them.

The overall pattern of the concentration time profiles was similar between the two polymorphs. After administration of either polymorph, absorption of NRD135S.E1 was rapid. Peak plasma concentrations were in many cases already achieved before or at the first sampling time point (0.25 h)

TABLE 4

| Parameter | Description of Parameter |
| --- | --- |
| Tmax | The time after dosing at which the maximum concentration was observed. |
| Cmax | The maximum concentration observed after dosing. |
| AUC(0–t) | The area under the concentration versus time curve (from 0 to time after dosing at which the last quantifiable concentration was observed) estimated by the linear trapezoidal method. |
| AUC(0–∞) | The area under the concentration versus time curve from time zero to infinity. |
| T½ | The apparent terminal elimination half-life. |
| AUCext % | The fraction of AUC0–∞ observed after the last measured concentration above the limit of quantification. |
| CL/F | The apparent clearance as determined after oral administration. |
| Vd/F | The apparent volume of distribution as determined after oral administration | and in no instance was Tmax longer than 0.5 h. Subsequently concentrations dropped rapidly to achieve a first trough concentration at around 4 hours which was at most ¹⁄₁₀ of initially achieved concentrations. After this time point—coincident with renewed access of the dogs to food—concentrations rose again to form a secondary (low) peak before declining again. The secondary concentration increases are suggestive of enterohepatic recirculation of the drug and have already been noted before in rats (see e.g. Study 12NVMDP1R1), dogs (see Study VPT1468), and humans (see Study NRD135S.E1.101). The irregularities in the concentration decline prevented accurate estimation of the elimination half-life. However, these terminal declines were often very similar for both polymorphs in the same animal lending support for an estimated mean half-life of NRD135S.E1 around 3-4 hours. As the extrapolated part of AUC(0–∞) was small (no more than 6%), AUC(0–∞) and with this the disposition parameters CL/F and V/F could still be reliably estimated. Both measures of exposure to the drug appeared to be higher after polymorph 2 than after polymorph 1. The least squares (LS) geometric mean estimate for the AUC(0–∞) (corrected to a 60.0 mg dose) for polymorph 1 (141232) was 13170 h·ng/mL, for polymorph 2 (COEN4-91-M) 20064 h·ng/mL. The corresponding $C_{max}$ values (corrected to a 60.0-mg dose) were 4986 ng/mL (polymorph 1) and 11088 ng/mL (polymorph 2) respectively. These differences between polymorphs are indicative of higher availability of NRD135S.E1 when polymorph 2 is given. Polymorph 2 is thermodynamically more stable than polymorph 1 and such a result would not have been expected.

The results of the statistical analyses are given in Table 6. Higher exposure was found for the NEW (polymorph 2) than for the OLD polymorph (polymorph 1). The least squares geometric mean estimate for the AUC extrapolated to infinity (corrected for dose)<AUCINF_obs_D> for the NEW was 1.52 times higher than for the OLD polymorph (90% CI: 1.35, 1.71); this difference was statistically significant (p=0.0016). The difference for maximum concentrations was even higher with a point estimate for the $C_{max}$ value (corrected for dose differences) for the NEW 2.22 fold (90% CI: 1.84; 2.70) higher than for the OLD polymorph. The results and conclusions from the analyses were not different, if the respective parameters were not corrected for dose differences or if unextrapolated AUC values were analyzed.

While there was clearly a difference in extent of absorption, there was no difference in rate of absorption between the two polymorphs as judged by the time needed to reach maximum concentrations ($T_{max}$). There were no differences in the elimination rate constant or half-life observed after the two polymorphs.

Concentration-time profiles of NRD135S.E1 after both polymorphs were characterized by rapid absorption and a sharp concentration decline after peak concentrations; secondary humps in the profiles at 4 hours and beyond were suggestive of entero-hepatic recirculation.

Measures of exposure to the drug, maximum observed concentration (Cmax) and area under the plasma concentration-time curve (AUC), appeared to be higher after polymorph 2 than after polymorph 1. Geometric mean ratios (polymorph 2/polymorph 1) of 1.52 (90% CI: 1.35, 1.71) for the AUC measure and of 2.22 (90% CI: 1.84; 2.70) for the Cmax measure resulted. The results and conclusions from the analyses were not different, if the respective parameters were not corrected for dose differences or if unextrapolated AUC values were analyzed. These differences between polymorphs are indicative of higher availability of NRD135S.E1 when polymorph 2 is given.

While there was clearly a difference in extent of absorption, there was no difference in rate of absorption between the two polymorphs as judged by the time needed to reach maximum concentrations ($T_{max}$) and there were no differences in the elimination rate constant or half-life observed after the two polymorphs.

A relevant though statistically not significant effect of sequence was observed for $C_{max}$ for the ratio sequence-1 vs. sequence-2 that was estimated as 1.38 (90% CI: 1.06, 1.79). This sequence effect detracts from the precision with which exposure differences between the two polymorphs can be estimated.

What is claimed is:

1. A polymorphic form of a compound having the formula:

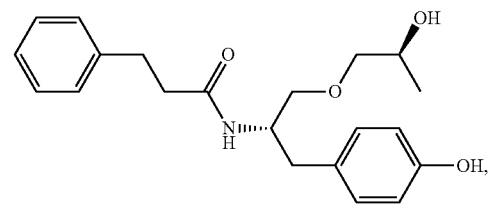

wherein the polymorphic form has a melting point in the range from about 105° C. to about 110° C.

2. The polymorphic form according to claim 1, wherein the polymorphic form has an X-ray powder diffraction pattern (CuKα) comprising a peak at 19.0±0.2 °2θ.

3. The polymorphic form according to claim 2, wherein the X-ray powder diffraction pattern (CuKα) further comprises one or more peaks selected from peaks at 11.25±0.2, 17.38±0.2, 17.57±0.2, 20.74±0.2, 20.91±0.2, 22.42±0.2, and 23.30±0.2 °2θ.

4. The polymorphic form according to claim 1, wherein the melting point is in a range of from about 106° C. to about 109° C. or about 107° C. to about 108° C.

5. The polymorphic form according to claim 1, having a melting enthalpy in a range of either 100 J/g to 140 J/g, 110 J/g to 130 J/g, or 115 to 125 J/g.

6. A medicament comprising the polymorphic form according to claim 1.

7. The medicament according to claim 6, in a product form configured for oral administration.

8. A pharmaceutical composition for use in the treatment or prophylaxis of pain, inflammation and/or autoimmunity, said composition comprising a pharmaceutically effective amount of a compound having the formula:

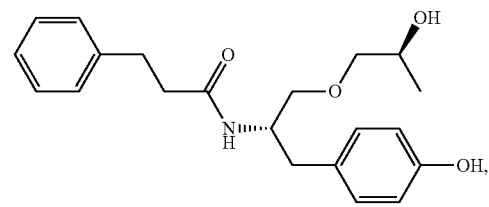 [SMILES: C[C@H](O)COC[C@H](Cc1ccc(O)cc1)NC(=O)CCc1ccccc1]

wherein the polymorphic form has a melting point in the range from about 105° C. to about 110° C.

9. The pharmaceutical composition according to claim 8, which includes one or more pharmaceutically acceptable excipients.

10. The pharmaceutical composition according to claim 8, wherein said composition is formulated as a unit dosage form comprising from 0.1 to about 500 mg of the compound.

11. The pharmaceutical composition according to claim 8, which is formulated for oral administration.

12. The pharmaceutical composition according to claim 8, wherein the melting point of the polymorphic form is in a range from about 106° C. to about 109° C. or about 107° C. to about 108° C.

13. The pharmaceutical composition according to claim 8, wherein the polymorphic form has an X-ray powder diffraction pattern (CuKα) comprising either a peak at 19.0±0.2 °2θ.

14. The pharmaceutical composition according to claim 13, wherein the X-ray powder diffraction pattern (CuKα) further comprises one or more peaks selected from peaks at 11.25±0.2, 17.38±0.2, 17.57±0.2, 20.74±0.2, 20.91±0.2, 22.42±0.2 and 23.30±0.2 °2θ.

15. The pharmaceutical composition according to claim 8, wherein the polymorphic form has a melting enthalpy within the range of either 100 J/g to 140 J/g, 110 J/g to 130 J/g or 115 to 125 J/g.

16. A method for treating or preventing pain, inflammation and/or autoimmunity in a human or non-human animal patient in need thereof, wherein the method comprises administering to said patient a therapeutic effective amount of at least one compound according to claim 1 or of a medicament that comprises said at least one compound.

17. The method according to claim 16, wherein a daily dose of 0.1 mg to 15 g of said at least one compound is administered.

18. The method according to claim 16, wherein said at least one compound is administered orally.

19. A method for treating or preventing pain, inflammation and/or autoimmunity in a human or non-human animal patient in need thereof, wherein the method comprises administering to said patient the pharmaceutical composition according to claim 8 containing a therapeutic effective amount of the at least one compound.

20. The method according to claim 19, wherein a daily dose of 0.1 mg to 15 g of said at least one compound is administered.

21. The method according to claim 19, wherein said pharmaceutical composition is administered orally.

22. The method according to claim 19, wherein the pharmaceutical composition includes one or more pharmaceutically acceptable excipients.

* * * * *